(12) United States Patent
Sorrentino et al.

(10) Patent No.: US 11,268,158 B2
(45) Date of Patent: Mar. 8, 2022

(54) ASSAY FOR SAFETY ASSESSMENT OF THERAPEUTIC GENETIC MANIPULATIONS, GENE THERAPY VECTORS AND COMPOUNDS

(71) Applicant: ST. JUDE CHILDREN'S RESEARCH HOSPITAL, INC., Memphis, TN (US)

(72) Inventors: Brian P. Sorrentino, Memphis, TN (US); Sheng Zhou, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 294 days.

(21) Appl. No.: 15/136,298

(22) Filed: Apr. 22, 2016

(65) Prior Publication Data
US 2016/0312304 A1    Oct. 27, 2016

Related U.S. Application Data

(60) Provisional application No. 62/152,340, filed on Apr. 24, 2015.

(51) Int. Cl.
C12Q 1/70    (2006.01)
(52) U.S. Cl.
CPC .................... *C12Q 1/702* (2013.01)
(58) Field of Classification Search
None
See application file for complete search history.

(56) References Cited

U.S. PATENT DOCUMENTS

| | | | |
|---|---|---|---|
| 7,575,925 B2 | 8/2009 | Schmitt et al. | |
| 8,772,028 B2 | 7/2014 | Zuniga-Pflucker et al. | |
| 2002/0168660 A1* | 11/2002 | Chen | C12N 5/0647 |
| | | | 435/6.11 |

OTHER PUBLICATIONS

Schmitt et al. (Immunity, vol. 17, 749-756, Dec. 2002) (Year: 2002).*
Holmes (Cold Spring Harb. Protoc, 4(2): 1-13, 2009). (Year: 2009).*
Hacein-Bey-Abina et al (Science, 302(5644): 415-419, 2003) (Year: 2003).*
Braun, Christian J. et al., "Gene Therapy for Wiskott-Aldrich Syndrome—Long-Term Efficacy and Genotoxicity", Sci. Transl. Med. (2014), vol. 6:227, p. 1-14.
Cattoglio, Claudia et al., "High-definition mapping of retroviral integration sites identifies active regulatory elements in human multipotent hematopoietic progenitors", Blood (2010), vol. 116:25, p. 5507-5517.
Cesana, Daniela et al., "Uncovering and Dissecting the Genotoxicity of Self-inactivating Lentiviral Vectors in Vivo", Mol. Ther. (2014), vol. 22:04, p. 774-785.

Dave, Utpal P. et al., "Murine Leukemias with Retroviral Insertions at Lmo2 Are Predictive of the Leukemias Induced in SCID-X1 Patients Following Retroviral Gene Therapy", PLoS Genetics (2009), vol. 05:05, e1000491.
Du, Yang et al., "Insertional mutagenesis identifies genes that promote the immortalization of primary bone marrow progenitor cells", Blood (2005), vol. 106:12, p. 3932-3939.
Du, Yang et al., "Cooperating cancer-gene identification through oncogenic-retrovirus-induced insertional mutagenesis", Blood (2005), vol. 106:07, p. 2498-2505.
Fatima, Soghra et al., "A Novel Saftey Assay for Retroviral Vectors That Reproduces Lmo2 Proto-Oncogene Insertional Activation Events", Molecular Therapy (2015), vol. 23, Supplement 1, Meeting Abstract 291, p. S117.
Hacein-Bey-Abina, Salima et al., "Insertional oncogenesis in 4 patients after retrovirus-mediated gene therapy of SCID-X1", The Journal of Clinical Investigation (2008), vol. 118:09, p. 3132-3142.
Hanawa, Hideki et al., "Extended ß-globin locus control region elements promote consistent therapeutic expression of a γ-globin lentiviral vector in murine ß-thalassemia", Blood (2004), vol. 104:08, p. 2281-2290.
Hawley, Robert G. et al., "Versatile retroviral vectors for potential use in gene therapy", Gene Therapy (1994), vol. 1, p. 136-138.
Holmes, Roxanne et al. "The OP9-DL1 System: Generation of T-Lymphocytes from Embryonic or Hematopoietic Stem Cells in Vitro", Cold Spring Harb. Protoc. (2009), doi:10.1101/pdb.prot5156, vol. 04:02, p. 1-12.
Homminga, Irene et al., "Integrated Transcript and Genome Analyses Reveal NKX2-1 and MEF2C as Potential Oncogenes in T Cell Acute Lymphoblastic Leukemia", Cancer Cell 19 (2011), p. 484-497.
Howe, Steven J. et al., "Insertional mutagenesis combined with acquired somatic mutations causes leukemogenesis following gene therapy of SCID-X1 patients", The Journal of Clinical Investigation (2008), vol. 118:09, p. 3143-3150.
Kodama, Hiroaki et al., "Involvement of the c-kit receptor in the adhesion of hematopoietic stem cells to stromal cells", Experimental Hematology (1994), vol. 22, p. 979-984.
Kuroda, Kazuki et al., "Delta-induced Notch Signaling Mediated by RBP-J Inhibits MyoD Expression and Myogenesis", The Journal of Biological Chemistry (1999), vol. 274:11, p. 7238-7244.
McCormack, Matthew P. et al. "The Lmo2 Oncogene Initiates Leukemia in Mice by Inducing Thymocyte Self-Renewal", Science (2010), vol. 327, p. 879-883.

(Continued)

*Primary Examiner* — Anoop K Singh
*Assistant Examiner* — Magdalene K Sgagias
(74) *Attorney, Agent, or Firm* — Troutman Pepper Hamilton Sanders LLP

(57) ABSTRACT

The invention is directed to methods of assessing the safety of therapeutic compounds and therapeutic genetic manipulations, including integrating gene therapy vectors and genome editing. In particular, the invention provides a method, wherein the oncogenic potential of therapeutic compounds and therapeutic genetic manipulations, including integrating gene therapy vectors and genome editing, is determined by determining the percentage of differentiation blocked hematopoietic progenitor cells.

13 Claims, 14 Drawing Sheets
(10 of 14 Drawing Sheet(s) Filed in Color)

Specification includes a Sequence Listing.

(56) References Cited

OTHER PUBLICATIONS

Modlich, Ute et al., "Cell-culture assays reveal the importance of retroviral vector design for insertional genotoxicity", Blood (2006), vol. 108:08, p. 2545-2553.

Modlich, Ute et al., "Insertional Transformation of Hematopoietic Cells by Self-inactivating Lentiviral and Gammaretroviral Vectors", Molecular Therapy (2009), vol. 17:11, p. 1919-1928.

Montini, Eugenio et al., "The genotoxic potential of retroviral vectors is strongly modulated by vector design and integration site selection in a mouse model of HSC gene therapy", The Journal of Clinical Investigation (2009), vol. 119:04, p. 964-975.

Montini, Eugenio et al., "Hematopoietic stem cell gene transfer in a tumor-prone mouse model uncovers low genotoxicity of lentiviral vector integration", Nature Biotechnology (2006), vol. 24:06, p. 687-696.

Pui, John C. et al., "Notch1 Expression in Early Lymphopoiesis Influences B versus T Lineage Determination", Immunity (1999), vol. 11, p. 299-308.

Ryu, Byoung Y. et al., "An experimental system for the evaluation of retroviral vector design to diminish the risk for proto-oncogene activation", Blood (2008), vol. 111:04, p. 1866-1875.

Shou, Yan et al., "Unique risk factors for insertional mutagenesis in a mouse model of XSCID gene therapy", Proc. Natl. Acad. Sci. USA (2006), vol. 103:31, p. 11730-11735.

Stein, Stefan et al., "Genomic instability and myelodysplasia with monosomy 7 consequent to EVI1 activation after gene therapy for chronic granulomatous disease", Nature Medicine (2010), vol. 16:02, p. 198-204.

Treanor, Louise M. et al., "Functional interactions between Lmo2, the Arf tumor suppressor, and Notch1 in murine T-cell malignancies", Blood (2011), vol. 117:20, p. 5453-5462.

Zhou, Sheng et al., "Quantitative Shearing Linear Amplification Polymerase Chain Reaction: An Improved Method for Quantifying Lentiviral Vector Insertion Sites in Transplanted Hematopoietic Cell Systems", Human Gene Therapy Methods (2015), vol. 26, p. 4-12.

Zhou, Sheng et al., "Mouse Transplant Models for Evaluating the Oncogenic Risk of a Self-Inactivating XSCID Lentiviral Vector", PLoS One (2013), vol. 08:04, e62333.

Zhou, Sheng et al., "Evaluating the Saftey of Retroviral Vectors Based on Insertional Oncogene Activation and Blocked Differentiation in Cultured Thymocytes", Molecular Therapy, The American Society of Gene & Cell Therapy (2016), p. 1-10 and Supplemental data.

\* cited by examiner

ASSAY FOR SAFETY ASSESSMENT OF THERAPEUTIC GENETIC MANIPULATIONS, GENE THERAPY VECTORS AND COMPOUNDS

CROSS-REFERENCE TO RELATED APPLICATIONS

This application claims priority from U.S. Provisional Application Ser. No. 62/152,340 filed on Apr. 24, 2015, which is incorporated herein by reference in its entirety.

STATEMENT AS TO FEDERALLY SPONSORED RESEARCH

This invention was made with government support under grants HL053749 and CA021765 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 24, 2016, is named 243734.000076_SL.txt and is 1,923 bytes in size.

FIELD OF THE INVENTION

The invention is directed to methods of assessing the safety of therapeutic compounds and therapeutic genetic manipulations, including integrating gene therapy vectors and genome editing. In particular, the invention provides a method, wherein the oncogenic potential of therapeutic compounds and therapeutic genetic manipulations, including integrating gene therapy vectors and genome editing, is determined by determining the percentage of differentiation blocked hematopoietic progenitor cells.

BACKGROUND OF THE INVENTION

Gene therapies with integrative vectors have demonstrated clinical benefits in treating various diseases including sickle cell anemia and immunodeficiencies, but the risk of insertional mutagenesis remains.

Gene therapies for X-linked severe combined immunodeficiency (X-SCID), Wiskott-Aldrich syndrome (WAS) and X-linked chronic granulomatous disease (X-CGD) with gammaretroviral vectors have caused a number of cases of acute lymphoid leukemias due to insertional activation of oncogenes, mostly LMO2 and myeloid leukemias due to insertional activation of MDS-EVI1, PRDM16, and MN1 [1-4]. Several cellular assays and mouse models have since been developed to assess the vector safety in terms of insertional mutagenesis [5-12]. However, none of these assays and models were able to reproduce the most relevant LMO2 vector integration and the results were mostly related to myeloid leukemias instead of lymphoid leukemias, while lymphoid leukemias occurred most frequently in gene therapy subjects.

SUMMARY OF THE INVENTION

As specified in the Background Section, there is a great need in the art to identify technologies for assessing the safety of therapeutic compounds and therapeutic genetic manipulations, including integrating gene therapy vectors and genome editing. The present invention addresses this and other needs by providing in vitro assays, wherein the oncogenic potential of therapeutic compounds and therapeutic genetic manipulations is determined by determining the percentage of differentiation blocked hematopoietic progenitor cells.

In one aspect, the invention provides a method for assessing oncogenic potential of a recombinant viral construct (e.g., a retroviral or lentiviral gene therapy vector) that integrates into a patient's (e.g., human) genome, said method comprising:
a) culturing hematopoietic progenitor cells under conditions that allow their development into mature hematopoietic cells;
b) transducing the hematopoietic progenitor cells with the recombinant viral construct;
c) continuing to culture the hematopoietic progenitor cells under conditions that allow their development into mature hematopoietic cells for about 10-40 days, and
d) determining the percentage of the hematopoietic progenitor cells blocked at an early differentiation stage relative to the total number of the hematopoietic progenitor cells, wherein the early differentiation stage is selected from the group consisting of DN1, DN2, DN3, and DN4.

In one embodiment, the method further comprises:
e) determining the relative oncogenic potential of the recombinant viral construct based on the percentage of the blocked cells determined in step (d). In one specific embodiment, the determination of the relative oncogenic potential in step (e) involves comparison to a predetermined standard or comparison to the percentage of the blocked cells determined for another construct using the same assay steps (a)-(d).

In one embodiment, the method further comprises isolating DNA from the blocked cells in step (d) and performing insertion site mapping. The presence of recurrent insertion sites can be used as further evidence that the construct is not safe for therapeutic use. The insertion site mapping can be performed, for example, using sequencing, quantitative shearing linear amplification PCR (qsLAM PCR), LAM-PCR, inverse PCR, and transposase-based methods.

In another aspect, the invention provides a method for assessing oncogenic potential of a compound or a genetic manipulation, said method comprising:
a) culturing hematopoietic progenitor cells under conditions that allow their development into mature hematopoietic cells;
b) exposing the hematopoietic progenitor cells to the compound or to the genetic manipulation;
c) continuing to culture the hematopoietic progenitor cells under conditions that allow their development into mature hematopoietic cells for about 10-40 days, and
d) determining the percentage of the hematopoietic progenitor cells blocked at an early differentiation stage relative to the total number of the hematopoietic progenitor cells, wherein the early differentiation stage is selected from the group consisting of DN1, DN2, DN3, and DN4.

In one embodiment, the above method further comprises:
e) determining the relative oncogenic potential of the compound or genetic manipulation based on the percentage of the blocked cells determined in step (d). In one specific embodiment, the determination of the relative oncogenic potential in step (e) involves comparison to a predetermined standard or comparison to the percentage of the blocked cells determined for another compound or genetic manipulation using the same assay steps (a)-(d).

In one embodiment of the above method, the genetic manipulation is a genome editing method. Non-limiting examples of encompassed genome editing methods include, e.g., methods which involve the use of Clustered Regularly Interspaced Short Palindromic Repeats (CRISPR)/Cas gene systems, methods which involve the use of zinc finger nucleases (ZFNs), methods which involve the use of transcription activator-like effector nucleases (TALENs), as well as methods which involve the use of any other nucleases that can cause DNA breaks or bind to DNA. For more information on suitable genome editing methods see, e.g., WO 2013163628, US 20140273235, EP 2336362, WO 2014093479, WO 2014089290, U.S. Pat. No. 8,795,965, US 20140357530, and WO 2011091324.

In one embodiment of any of the above methods of the invention, the determination of the percentage of the blocked cells in step (d) is performed using flow cytometry. In one embodiment of any of the above methods of the invention, the determination of the percentage of the blocked cells in step (d) is performed using fluorescence activated cell sorting (FACS).

In one embodiment of any of the above methods of the invention, the method further comprises isolating DNA from the blocked cells in step (d) and performing its analysis.

In one embodiment of any of the above methods of the invention, the method further comprises harvesting the hematopoietic progenitor cells prior to step (a).

In one embodiment of any of the above methods of the invention, the method further comprises isolating the hematopoietic progenitor cells prior to step (a).

In one embodiment of any of the above methods of the invention, the hematopoietic progenitor cells are cultured in steps (a) and (c) on a cell line that is adherent and promotes growth and differentiation of said hematopoietic progenitor cells.

Hematopoietic progenitor cells useful in the methods of the present invention include all clonogenic hematopoietic cells that can be differentiated in vitro and in which a differentiation block arises in response to oncogene activation or other deleterious genes such as, e.g., LMO2 and MEF2C. In one embodiment of any of the above methods of the invention, the hematopoietic progenitor cells are selected from the group consisting of thymocytes, bone marrow cells, CD34+ cells, and erythroid progenitor cells.

In one embodiment of any of the above methods of the invention, the hematopoietic progenitor cells are DN1 (CD4$^-$CD8$^-$CD25$^-$CD44$^+$)/DN2 (CD4$^-$CD8$^-$CD25$^+$CD44$^+$) early thymic progenitor (ETP) cells. In one specific embodiment, the ETP cells are cultured in steps (a) and (c) under conditions that allow development of ETP cells into mature CD4+/CD8+ thymocytes. In one specific embodiment, the blocked cells are DN2 (CD4$^-$CD8$^-$CD25$^+$CD44$^+$) ETP cells and step (d) involves determining the percentage of the DN2 (CD4$^-$CD8$^-$CD25$^+$CD44$^+$) ETP cells relative to the total number of the ETP cells. In one specific embodiment, the ETP cells are cultured in steps (a) and (c) on stroma cells (e.g., on OP9-DL1 stroma cells). In one specific embodiment, in step (c) the ETP cells are split every 3-5 days and seeded onto stroma cells at lower cell concentrations (e.g., 1-5×10$^5$ cells/ml). In another specific embodiment, the ETP cells are cultured in steps (a) and (c) in the presence of Notch signal (e.g., provided by an activated Notch ligand which can be, e.g., immobilized on culture plates). In one specific embodiment, the ETP cells are cultured in steps (a) and (c) in the presence of Flt3 ligand and IL-7. In one specific embodiment, the ETP cells are murine ETP cells (ETP cells from any mouse strain, including genetically modified mouse strains). In one specific embodiment, the murine ETP cells are from C57BL/6J mice.

In one specific embodiment, the invention provides a method for assessing oncogenic potential of a construct that integrates into a patient's genome, said method comprising:
a) culturing murine DN1 (CD4-CD8-CD25-CD44+)/DN2 (CD4-CD8-CD25+CD44+) early thymic progenitor (ETP) cells on OP9-DL1 stroma cells in the presence of Flt3 ligand and IL-7;
b) transducing the ETP cells with the construct;
c) continuing to culture the ETP cells on OP9-DL1 stroma cells in the presence of Flt3 ligand and IL-7 for about 10-40 days, splitting cells every 3-5 days and seeding onto OP9-DL1 stroma cells at 1-5×10$^5$ cells/ml, and
d) determining the percentage of the DN2 (CD4-CD8-CD25+CD44+) ETP cells relative to the total number of the ETP cells.

In one specific embodiment, the invention provides a method for assessing oncogenic potential of a compound or a genetic manipulation, said method comprising:
a) culturing murine DN1 (CD4-CD8-CD25-CD44+)/DN2 (CD4-CD8-CD25+CD44+) early thymic progenitor (ETP) cells on OP9-DL1 stroma cells in the presence of Flt3 ligand and IL-7;
b) exposing the ETP cells to said compound or genetic manipulation;
c) continuing to culture the ETP cells on OP9-DL1 stroma cells in the presence of Flt3 ligand and IL-7 for about 10-40 days, splitting cells every 3-5 days and seeding onto OP9-DL1 stroma cells at 1-5×10$^5$ cells/ml, and
d) determining the percentage of the DN2 (CD4-CD8-CD25+CD44+) ETP cells relative to the total number of the ETP cells.

These and other aspects of the present invention will be apparent to those of ordinary skill in the art in the following description, claims and drawings.

BRIEF DESCRIPTION OF THE DRAWINGS

This patent application file contains at least one drawing executed in color. Copies of this patent application with color drawing(s) will be provided by the Office upon request and payment of the necessary fee.

DETAILED DESCRIPTION OF THE INVENTION

Figure 1A:
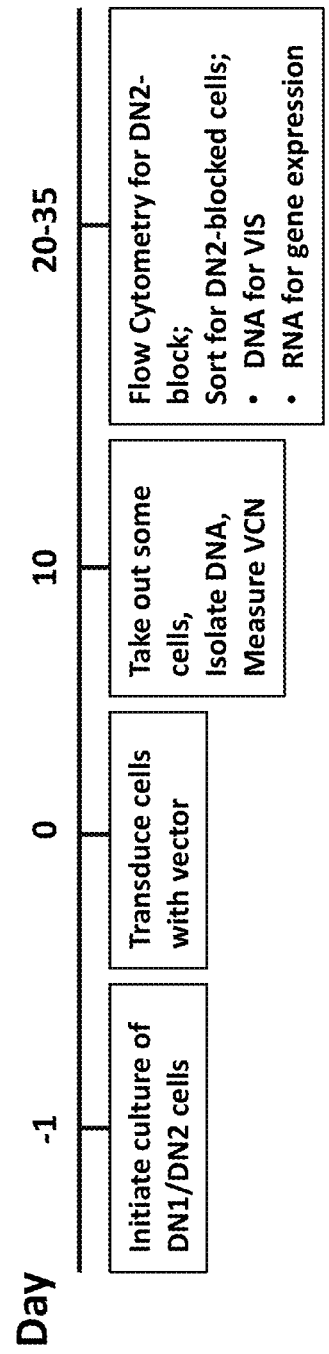
FIGS. 1A-1B. Gamma-retroviral vector transduction causes a DN2 differentiation block in cultured thymocytes. 1A. Schematic representation of the thymocytes transduction and culture time line. 1B. DN1/DN2 cells were transduced either with mock and MSCV-GFP vector and cultured on OP9-DL1 stromal cells for various period of time and cells were analyzed for differentiation stages by flow cytometry for CD44 and CD25 expression. DN2 blocked cells are CD44+/CD25+ in the upper right quadrant. The % of total cells in each quadrant are indicated. Note the accumulation of DN2 blocked cells in the MSCV-GFP group on day 22.

The present invention is based on the inventors' observation that transduction of murine early thymic progenitor (ETP) cells cultured on OP9-DL1 stroma cells with retroviral or lentiviral vectors that have oncogenic potential causes differentiation block of the ETP cells at the DN2 stage (CD4$^-$CD8$^-$CD25$^+$CD44$^+$). Based on this observation, the inventors developed a method, wherein the safety of gene therapy vectors and therapeutic compounds is determined by determining the percentage of differentiation blocked progenitor cells.

Definitions

As used herein, the terms "assessing therapeutic safety" and "assessing oncogenic potential" are used interchangeably and refer to the relative ability of a compound or a genetic manipulation (e.g., an integration of a gene therapy vector or genome editing) to cause an oncogenic transformation in hematopoietic cells. The methods of the invention provide a measure of the relative safety of various therapeutic compounds and therapeutic genetic manipulations (e.g., integrating gene therapy vectors and genome editing). For example, such methods can be used to compare the oncogenic potential of several different compounds or several different integrating recombinant viral constructs. The determination of whether or not these compounds or constructs are safe for clinical use would then depend on an assessment of the risk/benefit ratio considering such factors as, e.g., severity of the disease, patient condition, etc.

The term "hematopoietic progenitor cell" is used herein to refer to clonogenic hematopoietic cells that can be differentiated in vitro and in which a differentiation block arises in response to oncogene activation or other deleterious genes such as, e.g., LMO2, MEF2C. The progenitor cells useful in the methods of the invention include, without limitation, early thymic progenitor cells, thymocytes, bone marrow cells, CD34+ cells, and erythroid progenitors. The term "early thymic progenitor cell" or "ETP cell" refers to progenitor cells arising from the bone marrow, that seed the thymus and give rise to mature circulating thymocytes.

The term "stroma cells" is used herein to refer to an adherent cell line that can be grown in tissue culture experiments. The OP9-DL1 stroma cell line used in the Examples is a specific stroma cell line that expresses the Notch ligand and allows for the culture and development of primary thymocytes in tissue culture.

As used in this specification and the appended claims, the singular forms "a," "an," and "the" include plural references unless the context clearly dictates otherwise.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

As used herein, the terms "subject" or "patient" refer to any mammal. In a preferred embodiment, the subject or patient is human.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A practical Approach*, Volumes I and II (D. N. Glover ed. 1985); *Oligonucleotide Synthesis* (M J. Gait ed. 1984); *Nucleic Acid Hybridization* (B. D. Hames & S. J. Higgins eds. (1985); *Transcription and Translation* (B. D. Hames & S. J. Higgins, eds. (1984); *Animal Cell Culture* (R. I. Freshney, ed. (1986); *Immobilized Cells and Enzymes* (IRL Press, (1986); B. Perbal, *A Practical Guide To Molecular Cloning* (1984); F. M. Ausubel et al. (eds.), *Current Protocols in Molecular Biology*, John Wiley & Sons, Inc. (1994); among others.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1

Summary

Gene therapies for various immunodeficiencies have led to insertional activation of oncogenes, causing leukemias such as acute lymphoid leukemia and myeloid leukemias. The present example demonstrates the development of a novel sensitive cell-based assay to determine the safety of vectors used in gene therapies.

Gene therapies for X-linked severe combined immunodeficiency (SCID-X1) and Wiskott-Aldrich syndrome (WAS) with gammaretroviral vectors have caused a number of cases of acute lymphoid leukemias due to insertional activation of oncogenes, mostly LMO2. Transduction of murine bone marrow hematopoietic cells and subsequent culture for myeloid immortalization or transplant into recipient mice was able to detect the oncogenic activity of the spleen focus-forming virus (SFFV) vector, which was used in the WAS trial, but failed to detect the oncogenic activity of the SCID-X1 gene therapy vector MFG-γc. The lack of the most relevant Lmo2 insertion by gammaretroviral vectors in these assays demands more relevant and sensitive assays for vector safety assessment. It has been shown that murine early thymic progenitor cells (ETP), when cultured on OP9-DL1 stromal cells, progress through the DN1, DN2, DN3, DN4, DP and SP differentiation stages, and that overexpression of LMO2 in ETP cells caused a differentiation block at the DN2 stage ($CD4^-CD8^-CD25^+CD44^+$). The inventors tested whether transduction of ETP cells with gammaretroviral or lentiviral vectors could reproduce Lmo2 integrations and induce DN2 differentiation block. Three different gamma-retroviral vectors, MSCV-GFP, SFFV-GFP and MFG-γc, and two lentiviral vectors, Cl20-SFFV-mCherry and Cl20i4r-SFFV-mCherry, were tested. The two self-inactivating lentiviral vectors contain a single internal SFFV long terminal repeat but differ in that one contains the cHS400 chromatin insulators. ETP cells were transduced with these vectors and were cultured on OP9-DL1 cells for up to 40 days. The range of vector copy number was 1.07-10.78 for the MSCV-GFP vector, 0.24-1.22 for the SFFV-GFP vector, 0.59-7.98 for the MFG-γc vector, 3.97-13.04 for the Cl20-SFFV-mCherry vector and 4.57-18.21 for the Cl20i4r-SFFV-mCherry vector at days 10-11. Between days 20-35, a distinct DN2-blocked cell subpopulation was clearly detected by flow cytometry in all the 20 gamma-retroviral groups and also in 3/9 lentiviral groups. None of the 6 mock groups had any evidence of DN2 blockade. Insertion site mapping of sorted DN2 cells showed that in the 10 MSCV-GFP groups, 3 had Lmo2 insertions, 3 had Mef2c insertions, and 3 had both Lmo2 and mef2c insertions; in the 6 SFFV-GFP groups, 3 had Lmo2 insertions; in the 4 MFG-γc groups, 3 had Lmo2 insertions; both Cl20-SFFV-mCherry groups had Mef2c insertions and the one Cl20i4r-SFFV-mCherry group had Lmo2 insertion. These insertions occurred either in the introns or within +/−50 kb window of the gene. Transplant of the DN2-blocked cells from selected MSCV-GFP groups into recipient mice led to acute lymphoid leukemias. These results suggest that the transduction of ETP cells and the resultant DN2 blockade represent a more relevant and sensitive assay for vector safety assessment. These results further suggest that an ETP-like subpopulation may be present in the bone marrow of SCID-X1 and WAS patients and may explain the enhanced propensity of these disorders to oncogenic transformations.

Materials and Methods

Mice. P19Arf−/− mice were obtained from Dr. Charles Sherr's laboratory. The female C57BL/6J mice were purchased from Jackson Laboratory (Bar Harbor, Me.) and used at 4-6 weeks. Female IL2rg−/−Rag2−/− mice were purchased from Taconic Farms (Hudson, N.Y.) and used as transplant recipient at 6-14 weeks. All experimental procedures were reviewed and approved by the Institutional Animal Care and Use Committee of St Jude Children's Research Hospital.

Isolation of Thymocyte Subpopulations.

p19Arf−/− or C57BL/6J mice were sacrificed and thymi were harvested. Thymocytes were labeled with CD4-PE, CD8-PE and Ter119-PE antibodies (BD Biosciences) followed by incubation with anti-PE microbeads (Miltenyi). The $CD4^+$, $CD8^+$, $CD4^+CD8^+$, and $Ter119^+$ cells were depleted using MidiMacs columns and magnet (Miltenyi). The $CD4^-CD8^-$ cells were then labeled with CD4-APC-CY7, CD8-Alex-700, CD44-PE-Cy7 and CD25-APC Antibodies (BD Biosciences) and sorted for $CD44^+CD25^-$ DN1 and $CD44^+CD25^+$ DN2 cells using fluorescence activated cell sorter Typically about $5\times10^5$ DN1 and DN2 cells can be isolated from a single C57BL/6J mouse. The $CD44^+CD25^-$ DN1, CD44+CD25+ DN2, CD44−CD25+ DN3, CD44− CD25− DN4 and the CD4+CD8+ DP subpopulations were also directly sorted from fresh thymi cells and RNAs were extracted.

Vector Preparation.

The gammaretroviral vectors MSCV-GFP [13], SFFV-GFP [10] and MFG-rc [14] have been described previously and were produced from GPE-86 ecotropic producer cells (ATCC). The lentiviral vectors CL20-MSCV-mCherry, CL20-SFFV-mCherry and CL20i4r-SFFV-mCherry vectors were constructed using standard subcloning procedures and were transiently produced in 293T cells by cotransfecting with plasmids expressing ecotropic envelope protein, Gag-Pol and Rev-Tat. The MSCV element was released from the MSCV-GFP vector and the SFFV element was released from the SFFV-GFP vector by enzymatic digestion and ligated into the CL20 vector backbone [15] The ecotropic MSCV-Mef2c-Ires-GFP vector was produced transiently from 293T cells. All vectors were titered on NIH3T3 cells (ATCC).

Transduction of Cells with Vectors.

The stromal cell line expression cell surface notch ligand Delta-like 1 OP9-DL1 was obtained from J. C. Zuniga-Pflucker (University of Toronto, Toronto, Canada; can be also obtained from ATCC) and cultured in Alpha-MEM medium containing (Life Technologies) 20% fetal bovine serum according to the published method [16]. Briefly, OP9-DL1 cells can be generated as follows: OP9 cells (Kodama, H. et al., Exp. Hematol. 22, 979-984, 1994; can be obtained from the Riken Laboratory Cell Repository (Japan)) should be infected with the empty MigR1 retroviral vector (Pui et al., Immunity 11, 299-308, 1999) or with the MigR1 retroviral vector engineered to express the Delta-like-1 gene (Kuroda et al., J. Biol. Chem. 274, 7238-7244, 1999) 5' of the internal-ribosomal entry site, allowing the bicistronic expression of Delta-like-1 and green fluorescent protein (GFP). The MigR1 retroviral backbone can be obtained from W. Pear (University of Pennsylvania, PA). The retroviral vectors should be packaged using the PT67 retroviral packaging cell line (Clonetech-BD Biosciences). The Delta-like-1 gene containing a 3' T7 tag can be obtained T. Honjo (Kyoto University, Japan). Retrovirally transduced OP9 cells can be sorted on the basis of GFP expression, and expression of the Delta-like-1:T7 product can be determined by intracellular staining (Schmitt and Zúñiga-Pflücker Immunity 17, 749-756, 2002).

OP9-DL1 cells were seeded into each well of 12-well tissue culture plates. Two to four days later, when the OP9-DL1 cells have reached confluency, 5×10$^5$ freshly purified DN1/DN2 cells were inoculated into each well and prestimulated overnight in the presence of rmFlt3 (R&D Systems) (5 ng/ml) and rmIL7 (Peprotech) (1 ng/ml) in a total of 2 ml medium. The next day, 1 ml of supernatant was removed and vectors were added in a total volume of 1 ml, alone with 6 μg/ml polybrene (SIGMA) and rmFlt3 and rmIL7. The plates were centrifuged at 2000 rpm(g) for 1 hour at room temperature and then put back into the incubator. The next day, the medium was changed to fresh medium containing 5 ng/ml rmFlt3 and 0.2 ng/ml rmIL7. Every 3-6 days, up to 5×10$^5$ thymocytes were passaged onto to new 12-well plates that were preseeded with OP9-DL1 cells. At the second passage, the rmIL7 concentration was restored to 1 ng/ml.

Vector copy number assay. Ten days post transduction, cells were sorted for CD45+ thymocytes to eliminate contaminating OP9-DL1 stromal cells, which were also transduced with the vector due to the co-culture. DNA from sorted cells was extracted and the vector copy numbers in transduced cells were measured by quantitative realtime PCR as previously described [14].

Vector Insertion Site Analysis.

100 ng-1500 ng of genomic DNA from sorted DN2-blocked cells were used for mapping vector insertion sites using a quantitative shearing linear amplification PCR (qsLAM PCR) method [17] with the Illumina MiSeq instrument (Illumina Inc). The processed reads were mapped to Genome Reference Consortium Mouse Build 38 (mm10). Primer sequences for linear PCR were CCAATCAGTTCGCTTCTC (SEQ ID NO: 1) (MSCV and MFG vector), CTGCTTCTCGCTTCTGTTC (SEQ ID NO: 2) (SFFV vector), and AGTAGTGTGTGCCCGTCTGT (SEQ ID NO: 3) (CL20 and CL20i4r vector). Primer sequences for the final Nest-PCR were AATGA-TACGGCGACCACCGAGATCTACACTCTTTCCCTA-CACGACGCTCTTCCGATC TGCTGTTTG-CATCCGAATC (SEQ ID NO: 4) (MSCV vector), AATGATACGGCGACCACCGAGATCTA-CACTCTTTCCCTACACGACGCTCTTCCGATC TGTGGTCTCGCTGTTCCTT (SEQ ID NO: 5) (MFG and SFFV vector), and AATGATACGGCGACCACCGAGATC-TACACTCTTTCCCTACACGACGCTCTTCCGATC TGATCCCTCAGACCCTTTTAGT (SEQ ID NO: 6) (CL20 and CL20i4r vector).

qRT-PCR for Gene Expression.

Total RNAs were extracted from sorted DN2-blocked cells, fresh DN1, DN2, DN3, DN4, and DP subpopulations from wildtype thymus using the RNeasy Mini Kit (Qiagen) Reverse transcription was performed using the SuperScript VILO cDNA synthesis kit (Invitrogen). The Lmo2, Mef2c and Hhex transcript level were measured using qPCR method with corresponding Taqman gene expression assays (Invitrogen) and the StemOnePlus instrument (Invitrogen).

Mouse Transplant.

DN1/DN2 thymocytes from p19Arf−/− mice were transduced with the MSCV-Mef2c-Ires-GFP vector and cultured on OP9-DL1 stromal cells for 20 days. 1×10$^6$ cultured thymocytes were injected into each female recipient IL2rg−/−Rag2−/− mouse via lateral tail vein in a total volume of 0.5 ml PBS containing 2% fetal bovine serum. The recipient mice were irradiated for 600 rad in a Cesium137 irradiator 2 hours before injection.

Results

Transduction of DN1/DN2 Thymocytes with Gammaretrovial MSCV Vector Lead to Differentiation Block at the DN2 Stage.

Figure 1B:
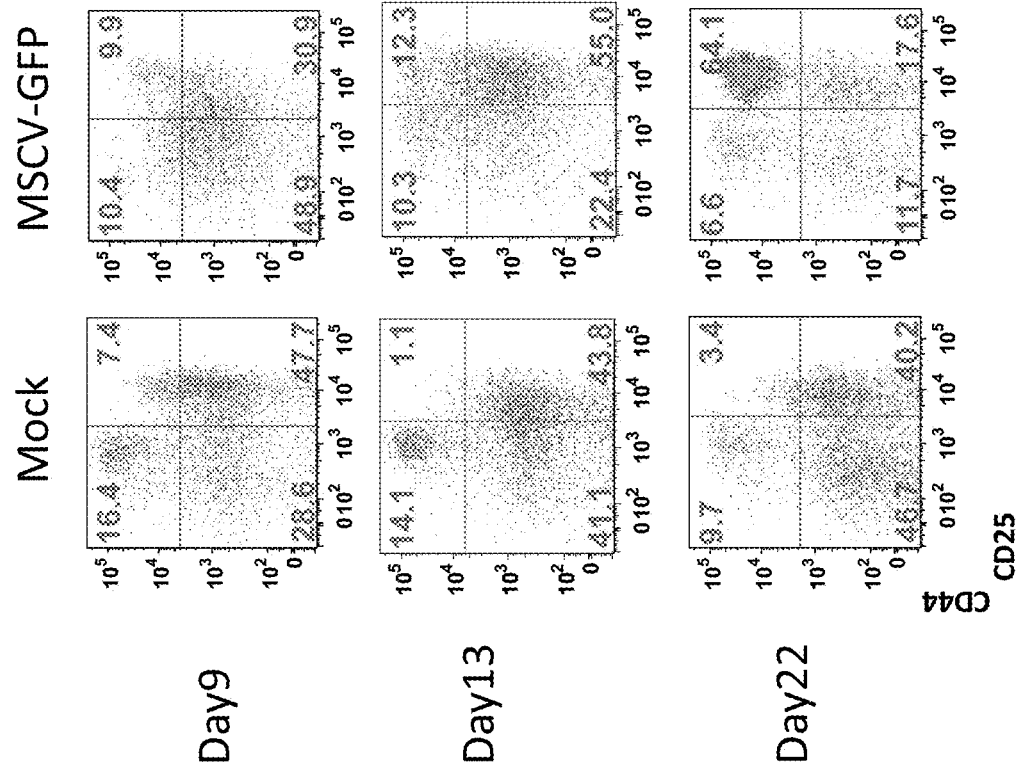
Figure 6:
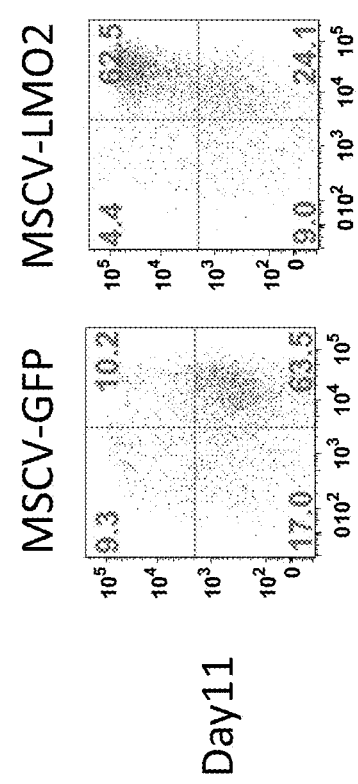
FIG. 6. Transduction of sorted DN1/DN2 cells. Sorted DN1/DN2 cells were transduced with a MSCV-LMO2-mCherry vector and showed that as much as 62.5% transduced cells in the CD4$^-$CD8$^-$ gate were blocked at the CD25$^+$CD44$^+$ DN2 stage as early as 11 days post transduction, showing that LMO2 expression itself is sufficient to induce a DN2-block.

The overall timeline for thymocyte culture was depicted in FIG. 1a. Sorted DN1/DN2 cells were transduced with a MSCV-LMO2-mCherry vector [18] and as much as 62.5% transduced cells in the CD4−CD8− gate were blocked at the CD25+CD44+ DN2 stage as early as 11 days post transduction (FIG. 6), showing that LMO2 expression itself is sufficient to induce DN2-block. The DN1/DN2 cells were then transduced with a MSCV-GFP [13] vector that does not carry any oncogene. Between day 9 and 13 post transduction, the percentage of cells in the DN2 gate was very low, despite high transduction efficiency of the cells (70%) (FIG. 1b). On day 22, a significant DN2 blocked subpopulation appeared (FIG. 1b). In contrast, no DN2 block ever occurred in the mock group during the entire culture period (FIG. 1b). Vector insertion site analysis of the DN2 blocked cells in the MSCV-GFP group showed three unique vector insertion sites (VIS), one in the intron of the camk2a gene, one at 1.8 kb upstream of the JunB gene and one at 22.6 kb upstream of the LMO2 gene. Since LMO2 overexpression by itself may be sufficient to cause the DN2 block, the DN2 block by the MSCV-GFP vector is most likely due to the insertional activation of the Lmo2 gene by the vector LTR enhancer. Transductions of thymocytes with a MSCV-JunB-GFP vector (constructed using the MSCV-GFP vector backbone and the JunB cDNA (OriGene)) did not lead to a DN2 block at day 10 in transduced cells, showing that JunB activation is likely not sufficient to cause DN2 block.

Transduction of DN1/DN2 Thymocytes with MFG-Rc Lead to DN2 Block.

Figure 2A:
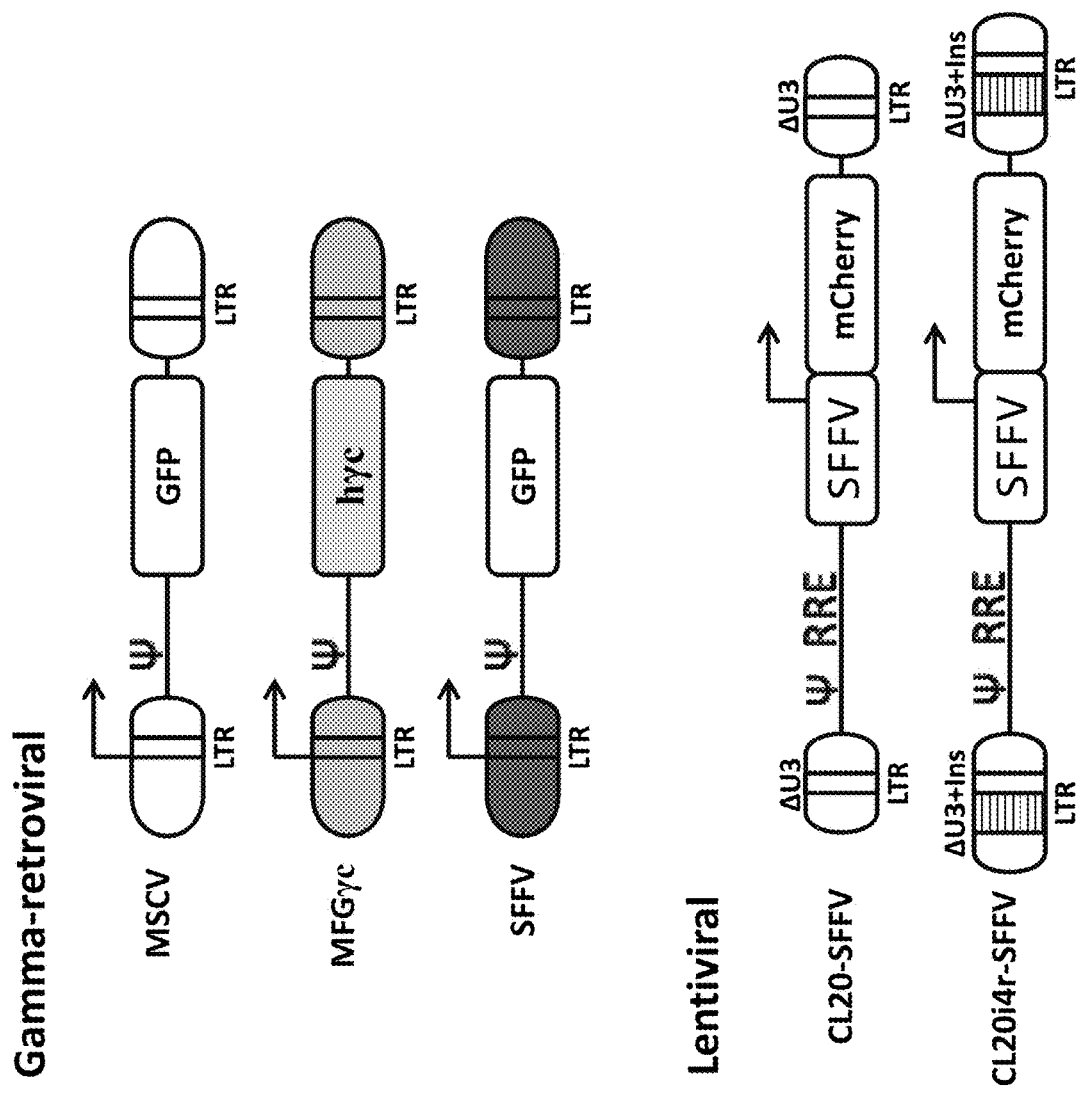
FIGS. 2A-2C. The MFG-γc vector and lentiviral vectors with internal LTR enhancer induce DN2 differentiation block in cultured thymocytes. 2A. Schematic representation of vectors used. 2B. DN1/DN2 cells were transduced with either Mock or the MFG-γc vector (n=3) and cultured for 28 days on OP9-DL1 stromal cells and then analysed for differentiation block by flow cytometry. The CD4$^-$CD8$^-$ subpopulations were first gated on (left panels) and displayed for the CD25 and CD44 expression (right panels). Vector copy number measured 10 days after transduction were listed as VCN on the right. Note the DN2 block occurring with the MFG-γc vector in the two higher copy number experiments. 2C. DN1/DN2 cells were transduced with either Mock, gamma-retroviral vector SFFV, self-inactivating lentiviral vector carrying an internal SFFV enhancer CL20-SFFV, and the same lentiviral vector with the 400 bp cHS chromatin insulator incorporated into the U3 region of the LTR and cultured for 32 days on OP9-DL1 stromal cells. Cell samples were taken at various time points and analyzed for differentiation status by flow cytometry. The CD4$^-$CD8$^-$ subpopulations were first gated on (left panels) and displayed for the CD25 and CD44 expression (right panels). In this experiment, DN2 blocked cells arose in all experimental arms but not in the Mock control.
Figure 2B:
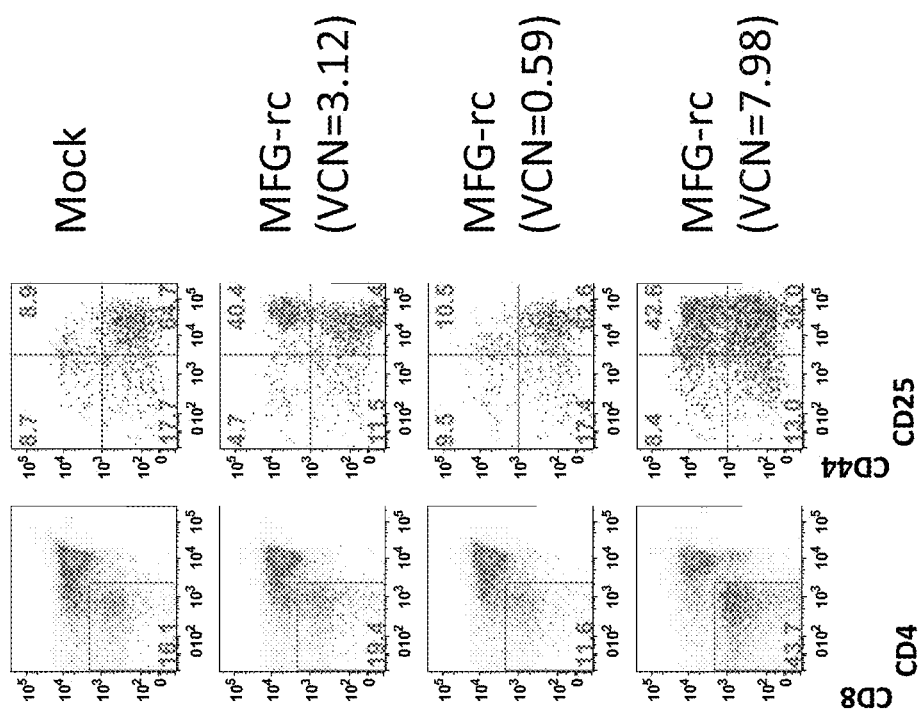

The inventors next tested whether the MFG-rc vector [14] could similarly cause a DN2 block in cultured DN1/DN2 cells (FIG. 2a). The MGF-rc vector has caused cases of leukemia in the SCID-X1 clinical studies [2,3] due to insertional activation of the LMO2 gene. Just like the MSCV-GFP vector, three out of four transductions with the MFG-rc vector caused a DN2 block in a significant subpopulation of cells by day 28 (FIG. 2b and Table 1). The transduction efficiency, as measured by vector copy number at day 10, was between 0.59-7.98 copies/cell (Table 1). The result demonstrates that the MFG-rc vector that was used in the clinical SCID-X1 gene therapy may indeed cause a differentiation block in cultured thymocytes.

Transduction of DN1/DN2 Thymocytes with Lentiviral Vectors Containing Internal Viral LTR Enhancers LED to a DN2 Block.

Figure 2C:
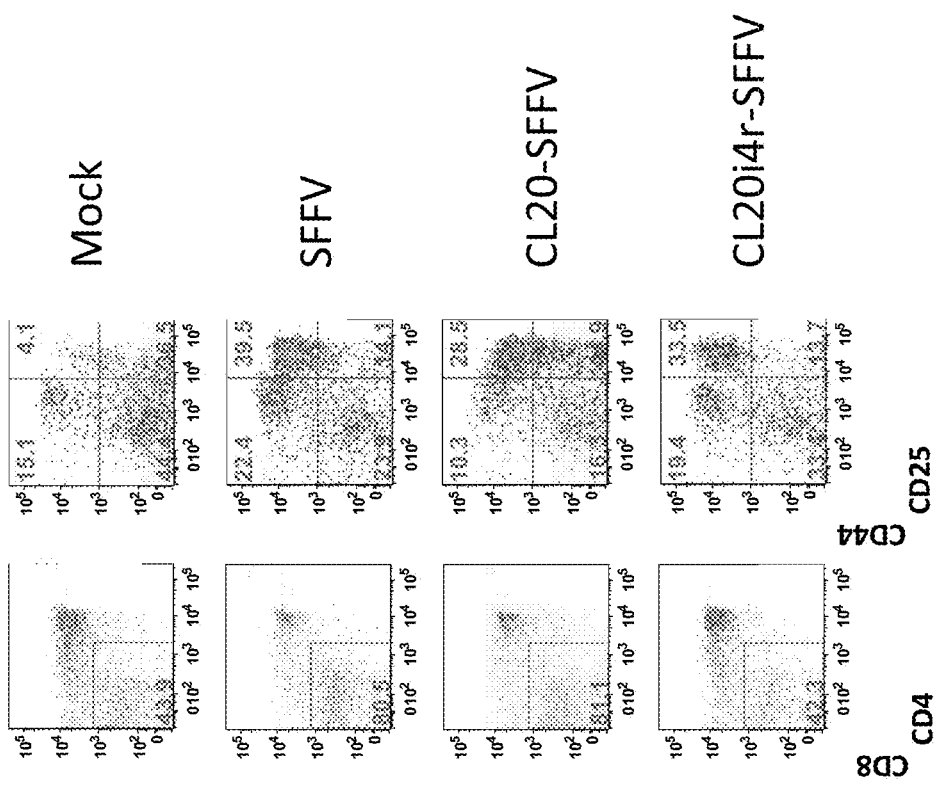
Figure 7:
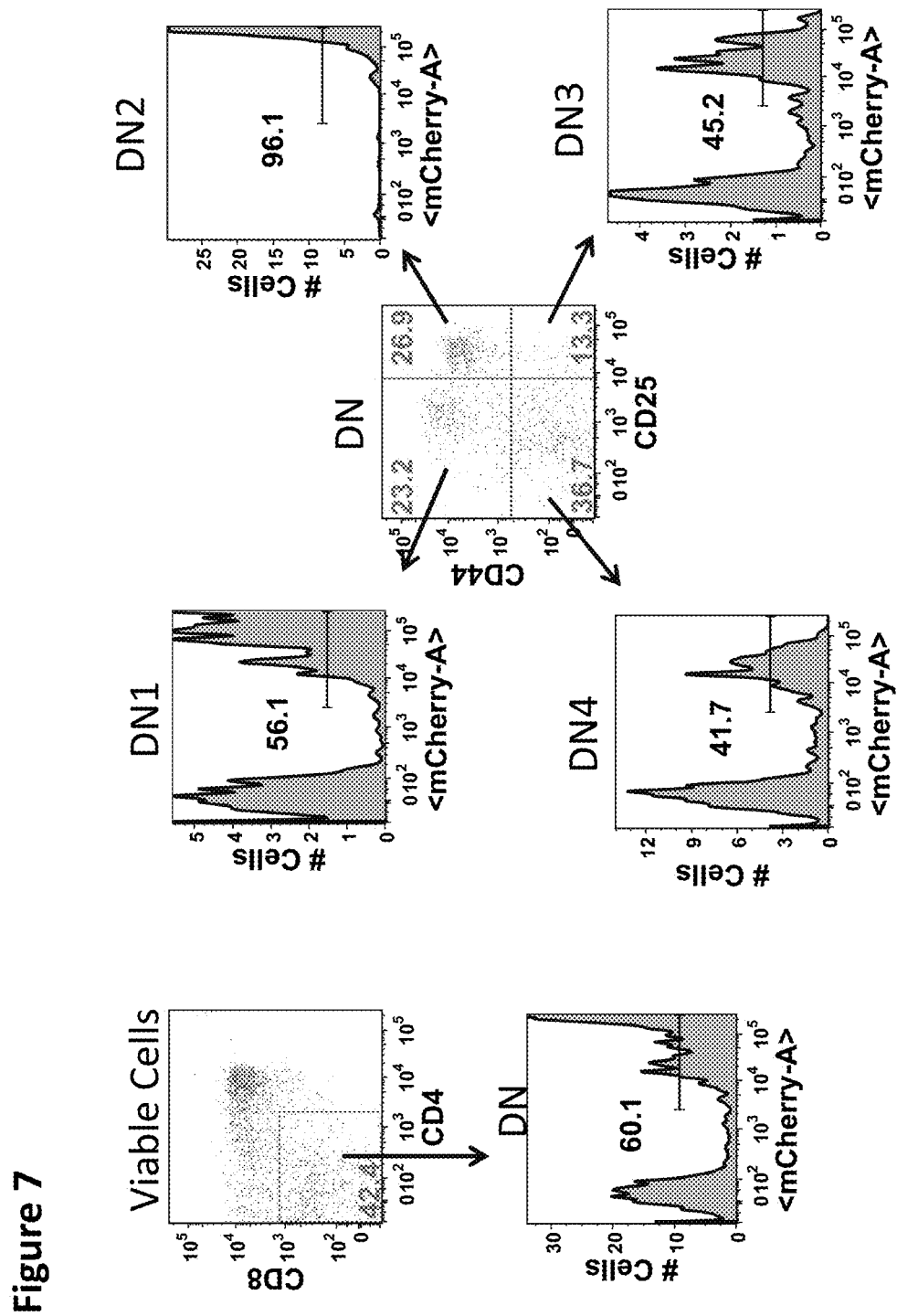
FIG. 7. DN2 blocked cells are highly enriched for vector-transduced cells. The cells in the DN1, DN2, DN3 and DN4 gates were analyzed for vector expression of the mCherry reporter gene. The DN2 blocked cells were highly enriched for the mCherry fluorescence, showing that the block is specific to transduced cells.

Since the gamma-retroviral vectors all have two copies of the strong LTR enhancers and thus may have strong insertional activation activity of adjacent genes, the inventors next tested whether a single copy of the SFFV LTR, or MSCV-LTR, when placed internally in a self-inactivating lentiviral vector, could cause a DN2 block in these cultured thymocytes (FIG. 2a). The inventors also tested whether bracketing the internal LTR with the 400 bp chicken beta globin chromatin insulator cHS400 [5] could reduce or eliminate the induction of the DN2 block (FIG. 2a). By day 32, a DN2 differentiation blocked subpopulation emerged in two of the three CL20-SFFV-GFP transductions and one of the three CL20i4r-SFFV-GFP transductions (FIG. 2c and Table 1). The DN2-blocked cells are highly enriched for the mCherry fluorescence (FIG. 7), further showing that the block is specific to transduced cells. The gamma-retroviral SFFV-GFP vector also caused a DN2 block in 6 of 6 independent transductions. The vector copy numbers with the lentiviral vectors at day 10 were overall higher than that in the gamma-retroviral vector transductions (Table 1). These results suggest that a single copy of the SFFV LTR in lentiviral vector can still cause a DN2 block, and the cHS400 chromatin insulator can further reduce but was not able to completely eliminate this effect.

Figure 3A:
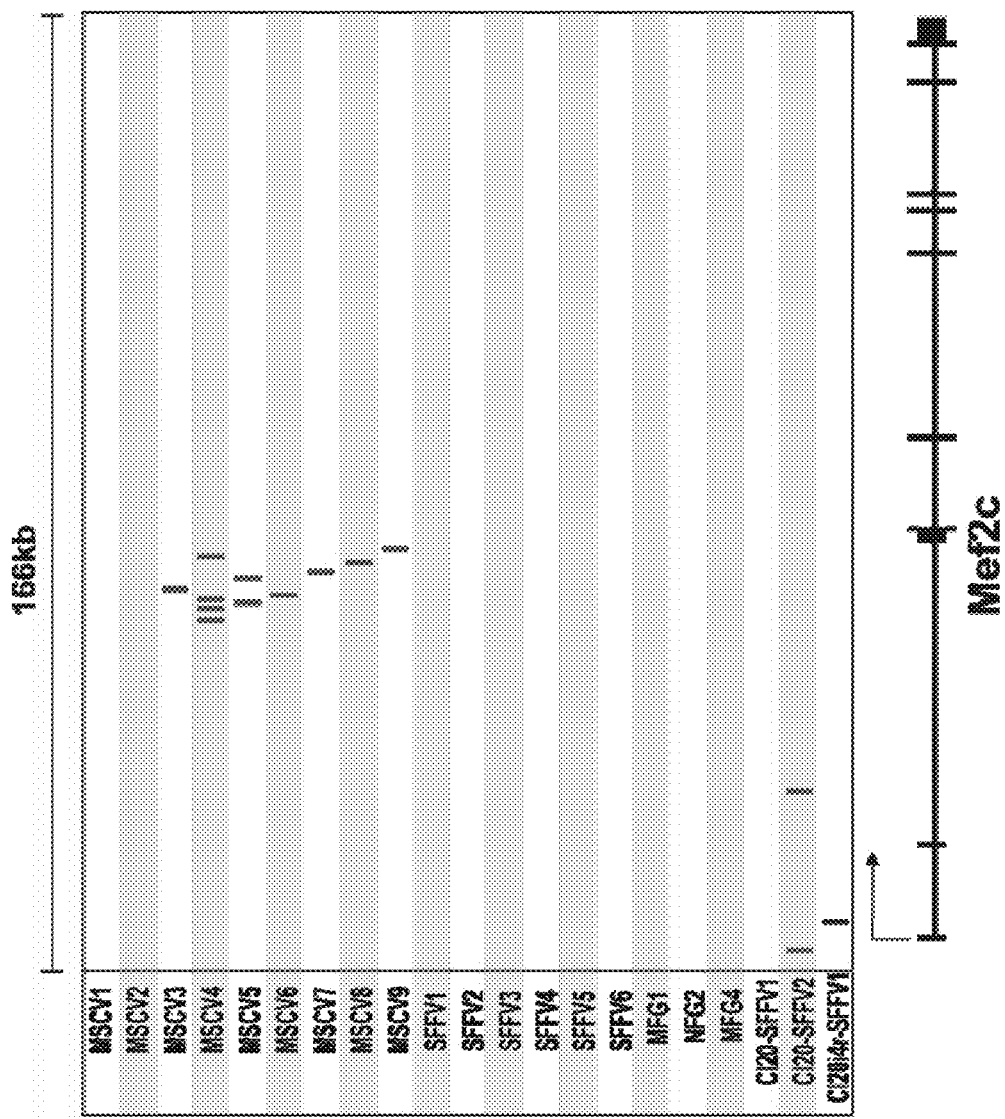
FIGS. 3A-3B. Recurrent vector insertion sites (VIS) in DN2 blocked cells. 3A. VIS in the Mef2c gene locus. The red lines show the vector insertion sites seen with the vectors displayed on the left hand column. 3B. VIS in the Lmo2 gene locus. Each vertical bar represents a unique insertion. The red bar denotes the same orientation of the vector with the gene. The black bar denotes the opposite orientation of the vector with the gene.
Figure 3B:
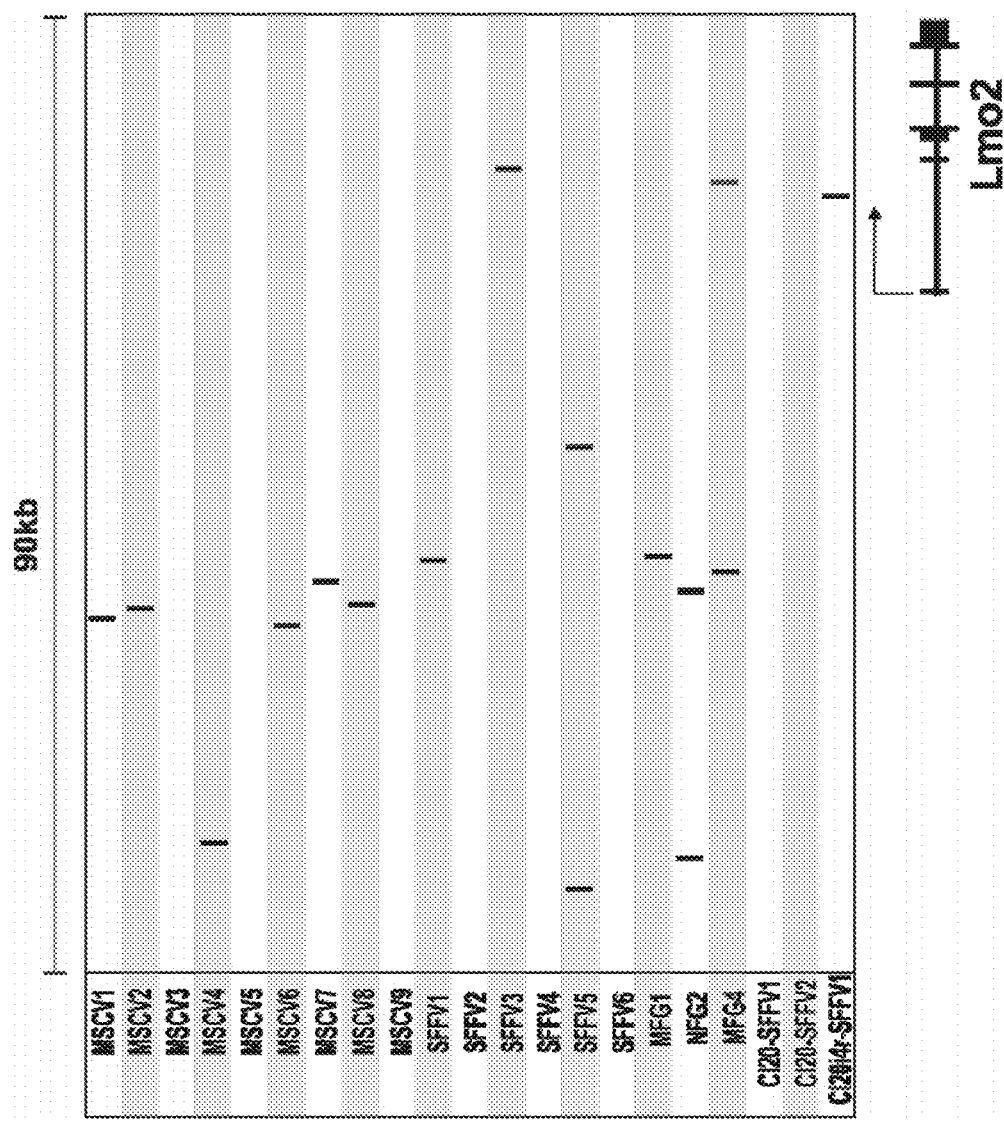

Recurrent Vector Insertions in the Lmo2 and Mef2c Gene Loci in the DN2 Blocked Cells. To determine what insertions may have caused the DN2 block in these cultures, the inventors sorted the DN2 blocked cells from 20 independent transductions of 6 different experiments, and mapped the vector insertion sites using a quantitative qsLAM PCR method [17]. Considering that the sorted DN2-blocked subpopulation could be contaminated by up to 10% of the non-specific background cells that linger in the DN2 gate, which are also seen in the Mock transduced group and that any VIS that caused the DN-block should be dominant in the sorted population, the VIS with a shear site count of ≥10 were considered in order to eliminate the irrelevant VIS from the contaminating cells. Based on this criterion, the total number of unique VIS among the 20 DN2-blocked samples are between 1-244 (Table 1). The inventors then searched for recurrent VIS, which are more likely to be the cause of the DN2 block. This analysis showed that Lmo2 and Mef2c are the only recurring VIS that occurred in more than three different samples. In majority of these samples, the count of shear sites for the Lmo2 or Mef2c insertion are within the top 10 insertions. In the 9 MSCV samples, two had single Lmo2 insertions, two had single Mef2c insertions, one had two Mef2c insertions, and 4 had both Lmo2 and Mef2c insertions. Three of the 6 SFFV samples had only Lmo2 insertions. Within the three MFG-rc samples, one had a single Lmo2 insertion, and the other two both had two Lmo2 insertions. One of the two CL20-SFFV-mCherry samples had a single Mef2c insertion and the other had two Mef2c insertions. The one CL20i4r-SFFV-mCherry sample had a single Lmo2 insertion. Interestingly, Mef2c insertions occurred only with the MSCV vector or with the lentiviral vector, but not with the SFFV and MFG-rc vectors, which is consistent with the lack of Mef2c insertions in the 5 cases of clinical leukemias with the MFG-rc vector. Four other insertions did not qualify as recurring VIS but are interesting. The Bcl2l11 and the Mvb12b intronic insertions are the only insertion in two separate SFFV samples. The Prdm16 intronic insertion occurred in another SFFV sample that lacks either Lmo2 or Mef2c insertions. The Ccnd3 intronic insertion occurred in one MSCV sample and one MFG-rc sample, along with the Mef2c and/or Lmo2 insertions. Two samples, which had high number of total VIS, are associated with 5 unique Lmo2/Mef2c insertions (MSCV4) and 4 Lmo2/Ccnd3 insertions (MFG-rc-1), suggesting that each of these insertions may represent different clones. All the Mef2c insertion sites with the MSCV vector are generally clustered in a 6 kb window upstream of the first coding exon, while insertion sites with the lentiviral vector are generally located in a 70 kb window around the first exon (FIG. 3a). Insertions in the Lmo2 gene occurred with all the different vector types and are primarily distributed in three clusters, in the first intron, in a 3 kb window 24 kb upstream of the first exon, and in a 3.5 kb window 60 kb upstream of the first exon (FIG. 3b). Given that some samples had either a single Lmo2 or single Mef2c insertion, the presence of multiple Lmo2 and/or Mef2c insertions in some samples can be best interpreted as evidence of independent clones in the DN2-blocked population.

Quantifying the Relative Insertional Mutagenesis Frequencies of Different Vectors.

Figure 4:
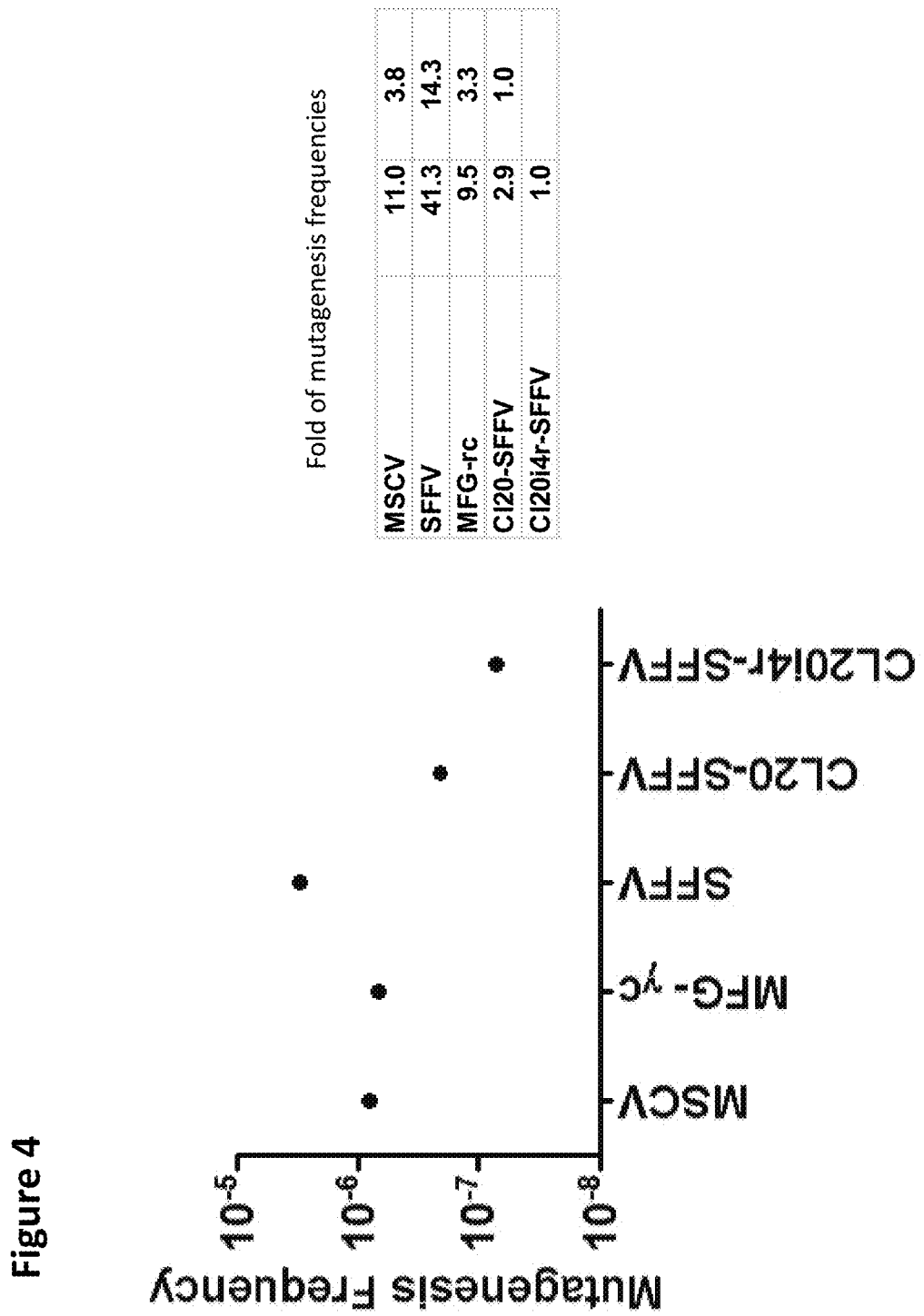
FIG. 4. Relative mutagenesis frequency associated with different vectors. The mutagenesis frequency is obtained by dividing the total number of recurrent VIS with a particular vector by the total number of VIS at day 10 post transduction as calculated by multiplying the vector copy number by the total cell number.
Figure 5:
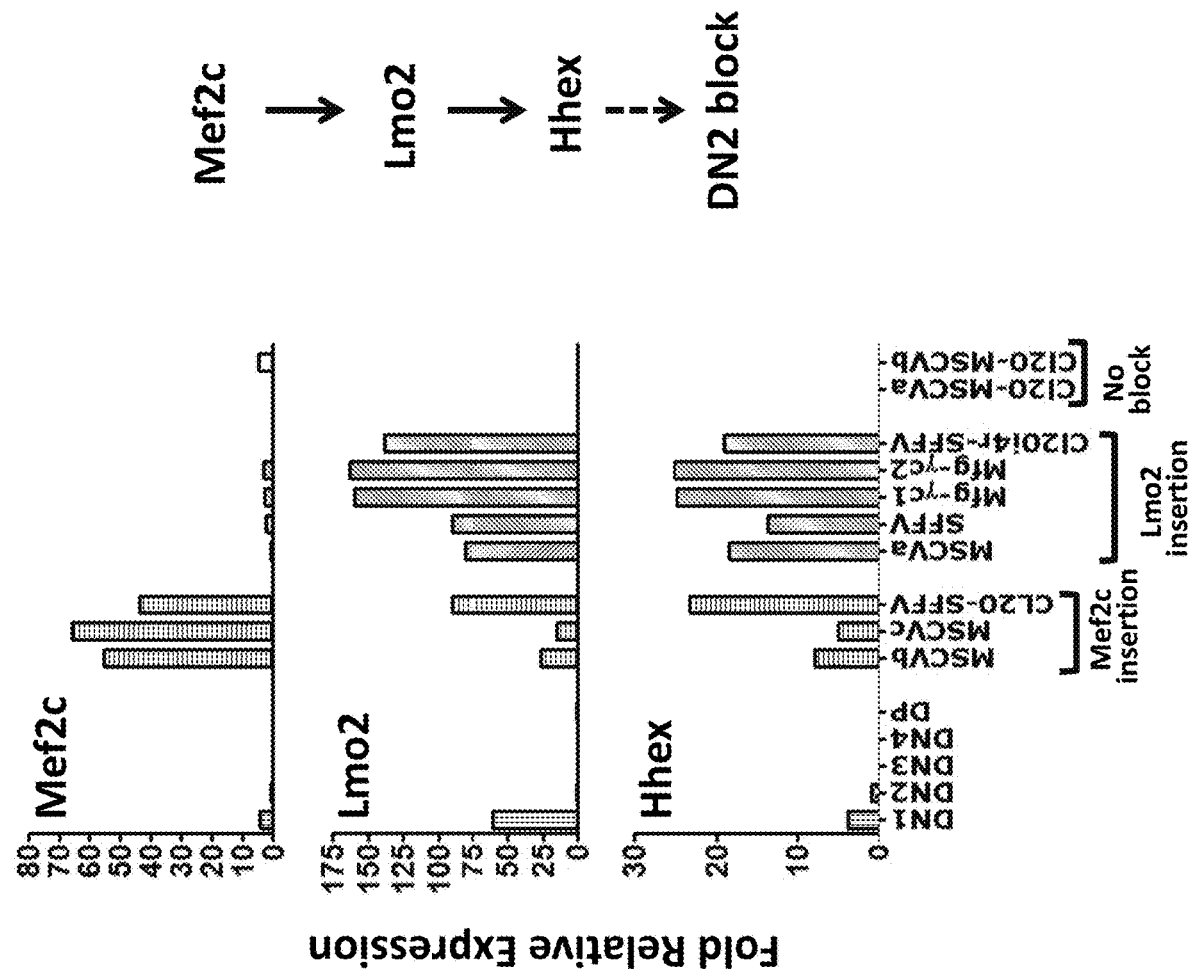
FIG. 5. Activation of oncogenes by vector insertion. RNA from sorted DN2-blocked cells from each sample was extracted and the expression of mRNA for the Mef2c, Lmo2 and Hhex genes was measured by quantitative PCR. The sorted DN1, DN2, DN3, DN4, DP cells from normal thymus were used as controls.

One way of comparing the relative safety of integrative vectors in this exemplary assay is to use the mutagenesis frequency, which can be calculated by dividing the total number of mutagenesis events by the total number of VIS. The total number of mutagenic events is the sum of unique recurrent VIS identified from the DN2-blocked cells, namely the Lmo2 and Mef2c insertions (as an exception, the Prdm16 and the Mvb12b insertions for the SFFV vector were also included), from all the samples that was tested with a particular vector. The total number of VIS is calculated by multiplying the average vector copy number obtained 10 days after transduction with the total number of cells at the transduction. Based on this calculation, the mutagenic activity of the SFFV, MSCV, MFG vectors are about 14.3, 3.8, 3.3 fold higher than that of the CL20 lentiviral vector that lacks an insulator (FIG. 4). For one mutagenic event to occur, it takes only 335,000 total insertions for the SFFV vector while it takes 4,785,750 total insertions for the Cl20-SFFV vector. By inclusion of the 400 bp cHS chromatin insulator, the safety of the vector is improved by about 2.9 fold, but may still cause a differentiation block due to insertional activation of Lmo2. For the CL20-MSCV vector, no DN2-block occurred in three transductions with a total number of 7421198 insertions, showing that a single copy of the MSCV LTR enhancer, when placed internally, is most likely safer than a single copy SFFV LTR enhancer in the lentiviral vector.

Mef2c and Lmo2 Expression are Upregulated by Vector Insertions.

To assess the effect of vector insertions on gene expression, the expression of Mef2c, Lmo2 and Hhex was measured in the sorted DN2-blocked cells harboring either the Lmo2 or the Mef2c insertion, but not both, by qRT-PCR method using Taqman gene expression assays and StepOne-Plus instrument (Invitrogen). These results were compared with the DN2 cells from wild type thymus (FIG. 4). In all the samples with only the Mef2c insertions that were measured, both Mef2c and Lmo2 are upregulated. In all the samples with only the Lmo2 gene insertions that were measured, the Lmo2 expression is dramatically upregulated, but Mef2c was not upregulated. In all the cases, the Hhex is upregulated and its expression level correlates very well with that of the Lmo2. These results demonstrate that the vector insertions most likely caused activation of the nearby gene and strongly suggest that upregulation of Lmo2 expression is caused by Mef2c, and that Hhex is a downstream target of Lmo2.

Overexpression of Mef2c in Thymocytes Lead to Early DN2 Block and Result in T-Cell Acute Lymphoblastic Leukemia (T-ALL) when Transplanted into Mice.

Figure 8:
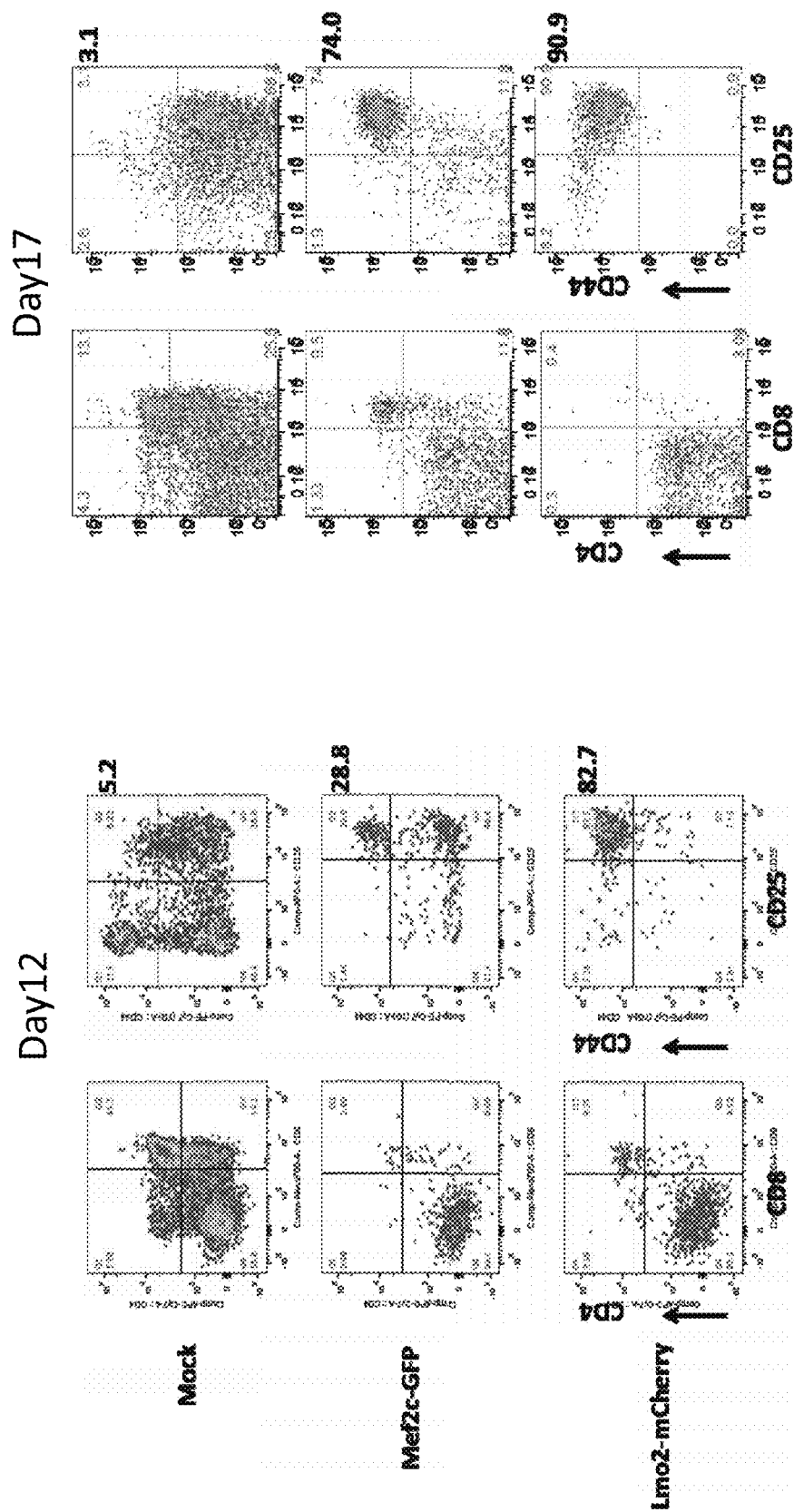
FIG. 8. A distinct DN2-blocked population can be seen in the Mef2c transduced cells. A MSCV vector was generated that expressed the Mef2c transgene along with a linked GFP gene. As early as 12 days after transduction with the Mef2c vector, a distinct DN2-blocked population could be seen, which further increased at day 17, demonstrating that Mef2c expression itself is sufficient to induce a DN2 block.
Figure 9:
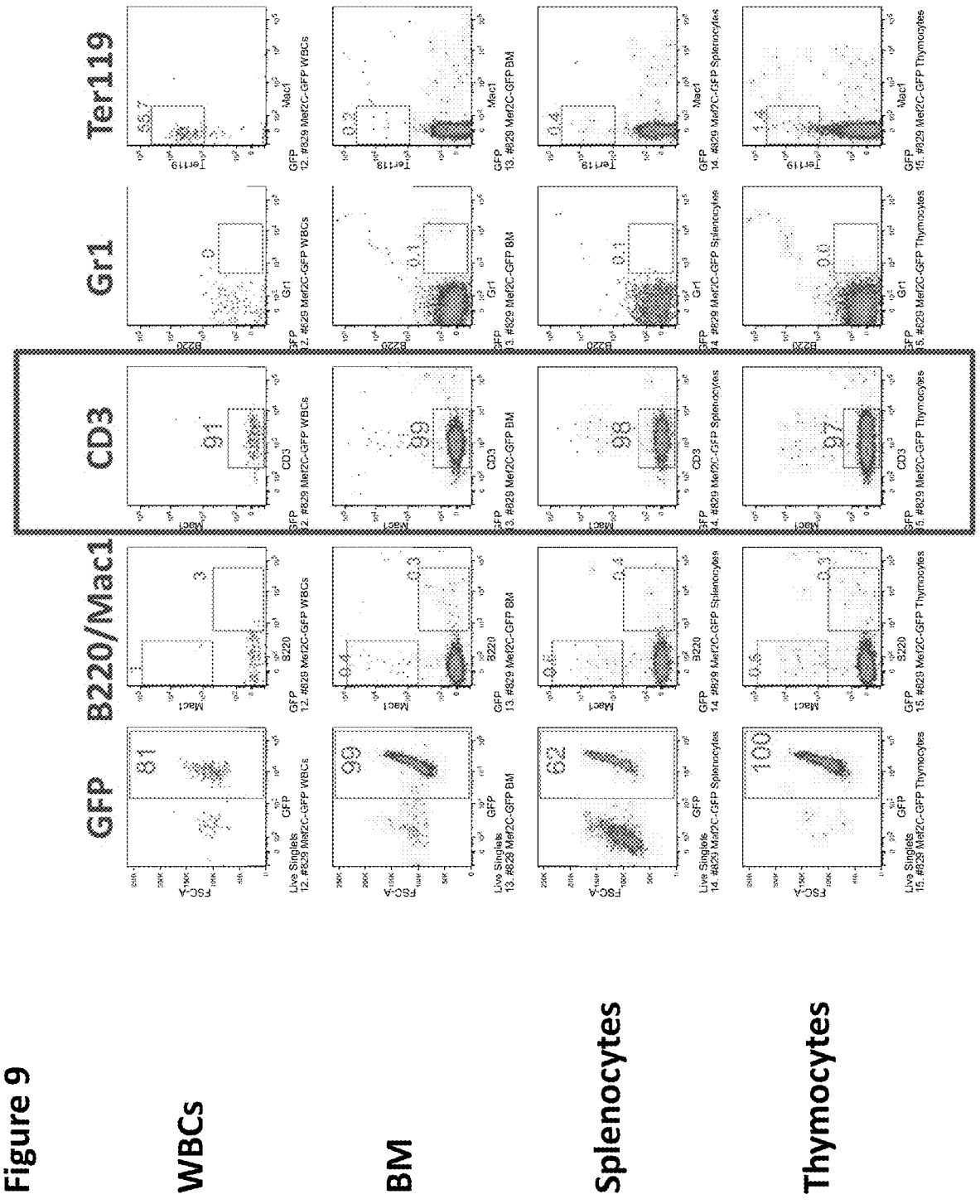
FIG. 9. Development of T-ALL in recipient mice transplanted with Mef2c-transduced thymocytes. 1×10$^6$ Mef2c transformed cells were transplanted into sublethally irradiated Rag2-/- IL2rg-/- Arf-/- recipient mice and the mice were observed for leukemogenesis. At 2 and 4 months post transplant, 2 of the 8 mice developed T-ALL as manifested by enlarged spleen (0.51 g and 0.49 g), high count of blood cells (49.6×10$^3$/μl and 35.2×10$^3$/μl), high number of CD3$^+$ cells in the bone marrow and in the peripheral blood, infiltration of CD3$^+$ leukemic cells in the liver and kidney (FIG. 10). This demonstrates that overexpression of Mef2c may cause a DN2-block in cultured thymocytes and may cause T-ALL when transplanted.
Figure 10:
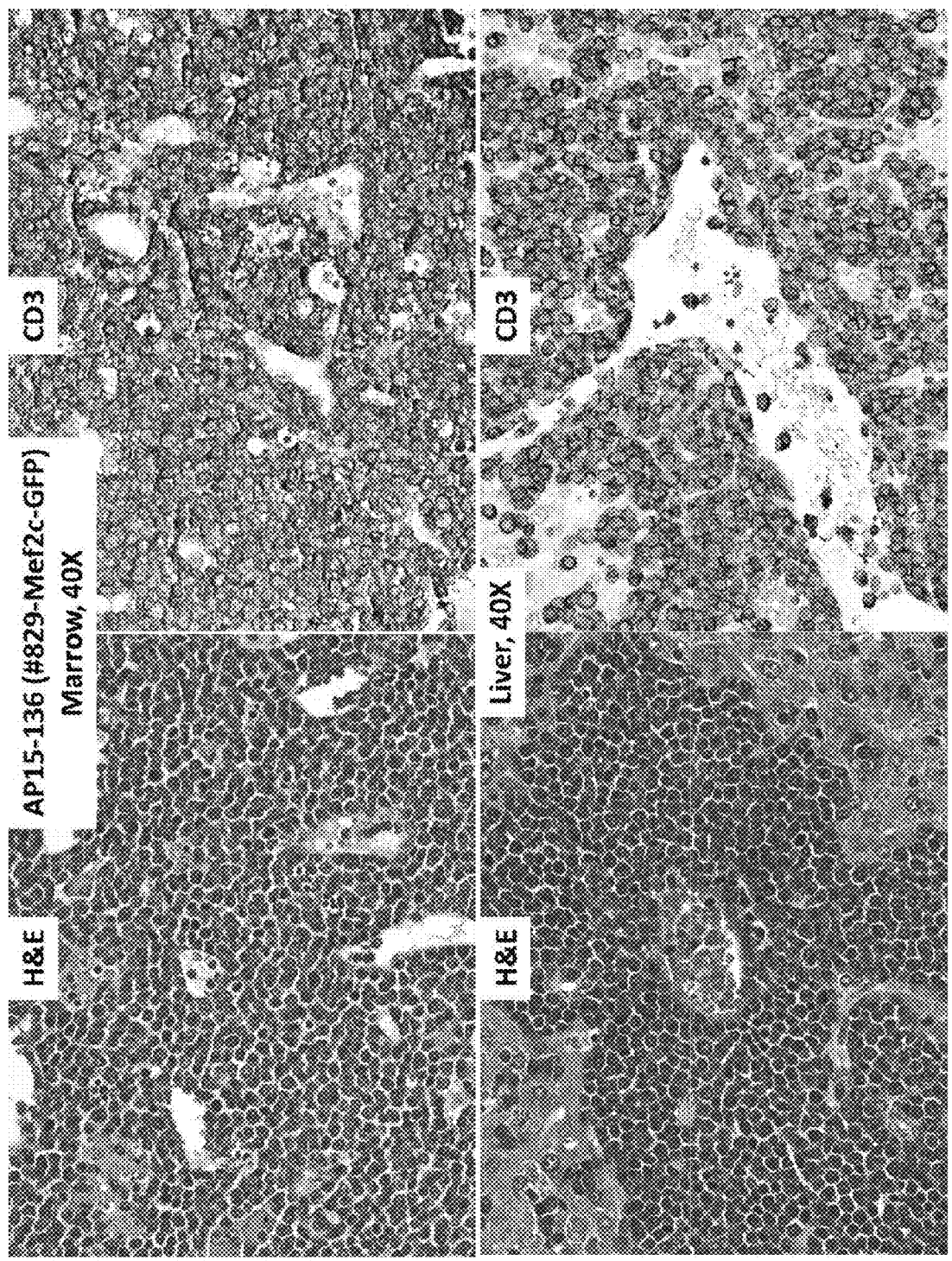
FIG. 10. Development of T-ALL in recipient mice transplanted with Mef2c-transduced cells. Depiction of infiltration of CD3$^+$ leukemic cells in the liver and kidney in the 2 mice demonstrating T-ALL.

It has been shown previously that overexpression of LMO2 in DN thymocytes from Arf−/− mice is sufficient to cause a DN2 block [18] and lymphoid leukemia when these cells are transplanted into recipient mice. To ascertain whether Mef2c activation was sufficient to induce DN2 block, DN1/DN2 cells from P19Arf−/− mice were transduced with a MSCV-Mef2c-GFP vector [19]. As early as 12 days after transduction, a distinct DN2-blocked population can be seen in the Mef2c transduced cells (FIG. 8), which further increased at day 17, demonstrating that Mef2c expression itself is sufficient to induce DN2 block. $1 \times 10^6$ cells were transplanted into sublethally irradiated Rag2−/− IL2rg−/− recipient mice, which were observed for leukemogenesis. At 2 and 4 months post transplant, 2 of the 8 mice had developed T-ALL as manifested by enlarged spleen (0.51 g and 0.49 g), high count of blood cells ($49.6 \times 10^3$ cells/μl and $35.2 \times 10^3$ cells/μl), high number of CD3$^+$ cells in the bone marrow and in the peripheral blood (FIG. 9), and infiltration of CD3$^+$ leukemic cells in the liver and kidney (FIG. 10). To the inventors' knowledge, this is the first demonstration that overexpression of Mef2c can cause a DN2-block in cultured thymocytes and can cause T-ALL when transplanted.

TABLE 1

Summary of the independent transduction experiments.

| Vector/ Sample ID | Transduc efficiency (VCN) | % GFP + at Day10 | % mCherry + at Day10 | Day of DN2 block | DN2 block (% DN2 cells) | Recurrent VIS (Other VIS) | Shear site rank | Total number of VIS |
|---|---|---|---|---|---|---|---|---|
| MSCV-GFP | | | | | | | | |
| MSCV1 | ND | 90.60 | N/A | 28 | Yes | 1 × Lmo2 | 8 | 14 |
| MSCV2 | ND | 68.90 | N/A | 22 | Yes | 1 × Lmo2 | 3 | 10 |
| MSCV3 | ND | 79.60 | N/A | 16 | Yes | 1 × Mef2c | 14 | 24 |
| MSCV4 | 6.52 | 94.0 | N/A | 20 | Yes (54.4%) | 4 × Mef2c, 1 × Lmo2 | 32, 31 | 123 |
| MSCV5 | 8.29 | 94.2 | N/A | 20 | Yes (51.5%) | 2 × Mef2c | 22 | 83 |
| MSCV6 | 1.89 | 64.6 | N/A | 20 | Yes (60.8%) | 1 × Mef2c, 1 × Lmo2 | 2, 12 | 12 |
| MSCV7 | 10.78 | 96.90 | N/A | 28 | Yes (82.6%) | 1 × mef2c, 1 × Lmo2 | 30 | 43 |
| MSCV8 | 4.33 | 80.90 | N/A | 28 | Yes (74.6) | 1 × Mef2c, 1 × Lmo2 | 8, 13 | 13 |
| MSCV9 | 2.19 | 56.40 | N/A | 28 | Yes (58.4%) | 1 × Mef2c | 2 | 3 |
| SFFV-GFP | | | | | | | | |
| SFFV1 | ND | 44.10 | N/A | 40 | Yes | 1 × Lmo2 | 1 | 1 |
| SFFV2 | ND | 63.30 | N/A | 28 | Yes | (Bcl2L11) | 1 | 1 |
| SFFV3 | ND | 28.90 | N/A | 22 | Yes | 1 × Lmo2 | 1 | 1 |
| SFFV4 | 1.22 | 64.8 | N/A | 24 | Yes (27.8%) | (Prdm16) | 2 | 4 |
| SFFV5 | 1.22 | 57.7 | N/A | 24 | Yes (40.8%) | 2 × Lmo2 | 2, 5 | 21 |
| SFFV6 | 0.24 | 17.4 | N/A | 24 | Yes (36.1%) | (Mvb12b) | 1 | 2 |
| MFG-γc | | | | | | | | |
| MFG-γc1 | ND | N/A | N/A | 22 | Yes (54.1%) | 1 × Lmo2 | 2 | 4 |
| MFG-γc2 | 3.12 | N/A | N/A | 28 | Yes (40.4%) | 2 × Lmo2 | 7, 15 | 17 |
| MFG-γc3 | 0.59 | N/A | N/A | 28 | No | | | |
| MFG-γc4 | 7.98 | N/A | N/A | 28 | Yes (42.6%) | 2 × Lmo2 | 5, 9 | 61 |
| CL20-MSCV- | | | | | | | | |

TABLE 1-continued

Summary of the independent transduction experiments.

| Vector/ Sample ID | Transduc efficiency (VCN) | % GFP + at Day10 | % mCherry + at Day10 | Day of DN2 block | DN2 block (% DN2 cells) | Recurrent VIS (Other VIS) | Shear site rank | Total number of VIS |
|---|---|---|---|---|---|---|---|---|
| mCherry | | | | | | | | |
| CL20-MSCV1 | 5.21 | N/A | 67.8 | 32 | No | | | |
| CL20-MSCV2 | 4.94 | N/A | 66.0 | 32 | No | | | |
| CL20-MSCV3 | 4.69 | N/A | 66.5 | 32 | No | | | |
| CL20-SFFV-mCherry | | | | | | | | |
| CL20-SFFV1 | 13.04 | N/A | 57.4 | 32 | Yes (29.7%) | 2 × Mef2c | 6 | 51 |
| CL20-SFFV2 | 11.71 | N/A | 39.4 | 24 | Yes (30.9%) | 1 × Mef2c | 2, 7 | 30 |
| CL20-SFFV3 | 3.97 | N/A | 31.0 | 32 | No | | | |
| CL20i4r-SFFV-mCherry | | | | | | | | |
| Cl20i4r-SFFV1 | 4.88 | N/A | 58.6 | 24 | Yes (35.4%) | 1 × Lmo2 | 4 | 16 |
| Cl20i4r-SFFV2 | 18.21 | N/A | 84.4 | 32 | No | | | |
| Cl20i4r-SFFV3 | 4.57 | N/A | 52.4 | 32 | No | | | |

Discussion

The present example demonstrates an application of a cellular assay that reliably reproduced the oncogenic Lmo2 insertion that occurred repeatedly in the SCID-X1 and WAS gene therapy with gamma-retroviral vectors. The assay utilizes the in vitro T lymphocyte differentiation system [16], and combines flow cytometry analysis for cell differentiation blocks and high-throughput quantitative vector insertion site mapping to confirm the presence of dominant oncogenic insertions, particularly Lmo2 and Mef2c. The assay is sensitive because it can detect the insertional activation of Lmo2 proto-oncogene by all gamma-retroviral vectors, including the MFG-rc vector that caused 4 cases of clinical leukemia due to LMO2 insertion [2,3]. The assay uses thymocytes from the commonly used wild type C57BL/6J mouse, takes about 35 days to complete and does not have to involve lengthy mouse transplantation. As the field is moving to lentiviral vectors, the exemplary assay also shows that the self-inactivating lentiviral vectors do integrate into the Lmo2 and the Mef2c loci, and activate those genes when strong internal enhancers such as SFFV are carried by the vectors. One key aspect of developing any new therapies is to properly assess their relative benefits and risks. A good assay should be sensitive enough to catch the dominant oncogenic activity of vectors and candidate therapeutic compounds, but should not be overly sensitive to prematurely eliminate otherwise safe and efficacious new therapies. The present assay meets both requirements for evaluating the relative safety of retroviral and lentiviral vectors and other integrative vectors developed for transducing hematopoietic cells to treat diseases, and any therapeutic genetic manipulations such as genome editing, as well as other candidate therapeutic compounds which may cause activation of oncogenes or other deleterious genes such as, e.g., LMO2, MEF2C.

The sensitivity of the present assay relies on two biological properties of the vectors: the integration of the vectors to proto-oncogenes and activation of those genes by the vectors to sufficient levels for the DN2 block to occur. It has been shown that lentiviral vectors integrate much less frequently into some oncogenes [20], especially LMO2, which may explain the much improved safety of lentiviral vectors in a number of safety assays. However, lentiviral vectors do integrate into proto-oncogenes such as Evi1 [10], and also can cause myeloid cell immortalization [10] in mouse hematopoietic cells. These lentiviral vectors are associated with myeloid leukemias in mouse models [7,8]. Consistent with these findings, the present assay shows that lentiviral vectors generally have about 3-14 fold less activity in inducing the DN2 differentiation block. The assay also demonstrates that lentiviral vectors do integrate into Lmo2 and Mef2c, which may cause their activation and associated DN2-block. The differentiation block that is induced by LMO2 overexpression has been associated with enhanced self-renewal of a subpopulation that is prone to other mutations, such as Notch1 activation, oncogenic translocations and loss of Cdkn2a, frequent secondary events in the clinical leukemia of gene therapy [2,3,21].

Using lymphoma prone AKXD mouse strain and replication competent gamma-retrovirus, Dave et al has shown that Lmo2 and Mef2c are recurring insertional genes in 5 lymphoid leukemias [22]. These insertions have been reproduced herein in an in vitro T cell differentiation assay that can be used for vector safety assessment, among other therapeutic compounds. The insertion into MEF2c was not yet seen in the clinical leukemias in gene therapy but was shown to be involved in clinical ETP-ALL through chromosomal translocations [23].

REFERENCES

1. Braun C J, Bortug K, Paruzynski A, Witzel M, Schwarzer A, et al. (2014) Gene therapy for Wiskott-Aldrich syndrome—long-term efficacy and genotoxicity. Sci Transl Med 6: 227ra233.
2. Hacein-Bey-Abina S, Garrigue A, Wang G P, Soulier J, Lim A, et al. (2008) Insertional oncogenesis in 4 patients after retrovirus-mediated gene therapy of SCID-X1. J Clin Invest 118: 3132-3142.
3. Howe S J, Mansour M R, Schwarzwaelder K, Bartholomae C, Hubank M, et al. (2008) Insertional mutagenesis combined with acquired somatic mutations causes leukemogenesis following gene therapy of SCID-X1 patients. JClinInvest 118: 3143-3150.
4. Stein S, Ott M G, Schultze-Strasser S, Jauch A, Burwinkel B, et al. (2010) Genomic instability and myelodysplasia with monosomy 7 consequent to EVI1 activation after gene therapy for chronic granulomatous disease. Nat Med 16: 198-204.
5. Ryu B Y, Evans-Galea M V, Gray J T, Bodine D M, Persons D A, et al. (2008) An experimental system for the evaluation of retroviral vector design to diminish the risk for proto-oncogene activation. Blood 111: 1866-1875.
6. Montini E, Cesana D, Schmidt M, Sanvito F, Bartholomae C C, et al. (2009) The genotoxic potential of retroviral vectors is strongly modulated by vector design and integration site selection in a mouse model of HSC gene therapy. JClinInvest 119: 964-975.
7. Montini E, Cesana D, Schmidt M, Sanvito F, Ponzoni M, et al. (2006) Hematopoietic stem cell gene transfer in a tumor-prone mouse model uncovers low genotoxicity of lentiviral vector integration. Nat Biotechnol 24: 687-696.
8. Cesana D, Ranzani M, Volpin M, Bartholomae C, Duros C, et al. (2014) Uncovering and dissecting the genotoxicity of self-inactivating lentiviral vectors in vivo. Mol Ther 22: 774-785.
9. Shou Y, Ma Z, Lu T, Sorrentino B P (2006) Unique risk factors for insertional mutagenesis in a mouse model of XSCID gene therapy. Proc Natl Acad Sci USA 103: 11730-11735.
10. Modlich U, Navarro S, Zychlinski D, Maetzig T, Knoess S, et al. (2009) Insertional transformation of hematopoietic cells by self-inactivating lentiviral and gammaretroviral vectors. Mol Ther 17: 1919-1928.
11. Modlich U, Bohne J, Schmidt M, von Kalle C, Knoss S, et al. (2006) Cell-culture assays reveal the importance of retroviral vector design for insertional genotoxicity. Blood 108: 2545-2553.
12. Du Y, Jenkins N A, Copeland N G (2005) Insertional mutagenesis identifies genes that promote the immortalization of primary bone marrow progenitor cells. Blood 106: 3932-3939.
13. Hawley R G, Lieu F H, Fong A Z, Hawley T S (1994) Versatile retroviral vectors for potential use in gene therapy. Gene Ther 1: 136-138.
14. Zhou S, Ma Z, Lu T, Janke L, Gray J T, et al. (2013) Mouse transplant models for evaluating the oncogenic risk of a self-inactivating XSCID lentiviral vector. PLoS One 8: e62333.
15. Hanawa H, Hargrove P W, Kepes S, Srivastava D K, Nienhuis A W, et al. (2004) Extended beta-globin locus control region elements promote consistent therapeutic expression of a gamma-globin lentiviral vector in murine beta-thalassemia. Blood 104: 2281-2290.
16. Holmes R, Zuniga-Pflucker J C (2009) The OP9-DL1 system: generation of T-lymphocytes from embryonic or hematopoietic stem cells in vitro. Cold Spring Harb Protoc 2009: pdb prot5156.
17. Zhou S, Bonner M A, Wang Y D, Rapp S, De Ravin S S, et al. (2015) Quantitative shearing linear amplification polymerase chain reaction: an improved method for quantifying lentiviral vector insertion sites in transplanted hematopoietic cell systems. Hum Gene Ther Methods 26: 4-12.
18. Treanor L M, Volanakis E J, Zhou S, Lu T, Sherr C J, et al. (2011) Functional interactions between Lmo2, the Arf tumor suppressor, and Notch1 in murine T-cell malignancies. Blood 117: 5453-5462.
19. Du Y, Spence S E, Jenkins N A, Copeland N G (2005) Cooperating cancer-gene identification through oncogenic-retrovirus-induced insertional mutagenesis. Blood 106: 2498-2505.
20. Cattoglio C, Pellin D, Rizzi E, Maruggi G, Corti G, et al. (2010) High-definition mapping of retroviral integration sites identifies active regulatory elements in human multipotent hematopoietic progenitors. Blood 116: 5507-5517.
21. McCormack M P, Young L F, Vasudevan S, de Graaf C A, Codrington R, et al. (2010) The Lmo2 oncogene initiates leukemia in mice by inducing thymocyte self-renewal. Science 327: 879-883.
22. Dave U P, Akagi K, Tripathi R, Cleveland S M, Thompson M A, et al. (2009) Murine leukemias with retroviral insertions at Lmo2 are predictive of the leukemias induced in SCID-X1 patients following retroviral gene therapy. PLoS Genet 5: e1000491.
23. Homminga I, Pieters R, Langerak A W, de Rooi J J, Stubbs A, et al. (2011) Integrated transcript and genome analyses reveal NKX2-1 and MEF2C as potential oncogenes in T cell acute lymphoblastic leukemia. Cancer Cell 19: 484-497.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. An in vitro method for assessing oncogenic potential of a recombinant viral construct that integrates into a patient's genome, said method comprising:
   a) transducing CD4-CD8-CD25-CD44+ (DN1) and/or CD4-CD8-CD25+CD4430 (DN2) early thymic progenitor (ETP) cells with the recombinant viral construct;
   b) culturing the cells transduced in step (a) under conditions that allow their development into mature CD4+-CD8+, CD4-CD8+or CD4+CD8- hematopoietic cells for about 10-40 days;
   c) identifying cells blocked at an early differentiation stage, wherein the early differentiation stage is selected from the group consisting of (DN1), (D2), CD4-CD8-CD44- CD25+(DN3), and CD4-CD8-CD44-CD25- (DN4):
   d) performing gene expression analysis and/or insertion site analysis of the blocked cells in step c), wherein the presence of recurrent insertion sites is used as evidence that the recombinant viral construct is not safe for therapeutic use, and
   e) determining the oncogenic potential of the recombinant viral construct based on the gene expression analysis and/or insertion site analysis in step (d) and/or based on the percentage of the blocked cells in step (c) relative to the total number of cells in culture.

2. The method of claim 1, wherein the determination of the oncogenic potential in step (e) involves comparison to a predetermined standard or to cultured ETP cells which have not been transduced with the recombinant viral construct.

3. The method of claim 1, wherein the construct is a retroviral or lentiviral gene therapy vector.

4. The method of claim 1, wherein the patient is human.

5. The method of claim 1, wherein the insertion site analysis in step (d) is performed using a method selected from the group consisting of sequencing, quantitative shearing linear amplification PCR (qsLAM PCR), LAM-PCR, inverse PCR, and transposase-based methods.

6. The method of claim 1, wherein the identification of the blocked cells in step (c) is performed using flow cytometry or fluorescence activated cell sorting (FACS).

7. The method of claim 1, wherein step (d) comprises isolating DNA or RNA from the blocked cells and performing its analysis.

8. The method of claim 1, further comprising harvesting and/or isolating the ETP cells prior to step (a).

9. The method of claim 1, wherein the cells in step (b) are cultured on a cell line that is adherent and promotes growth and differentiation of said cells.

10. The method of claim 1, wherein the cells in step (b) are cultured in the presence of Notch signal.

11. The method of claim 1, wherein the cells in step (b) are cultured in the presence of Flt3 ligand and IL-7.

12. The method of claim 1, wherein the ETP cells are murine ETP cells.

13. The method of claim 1, wherein the early differentiation stage in step (c) is DN2.

* * * * *

UNITED STATES PATENT AND TRADEMARK OFFICE
CERTIFICATE OF CORRECTION

PATENT NO. : 11,268,158 B2
APPLICATION NO. : 15/136298
DATED : March 8, 2022
INVENTOR(S) : Brian P. Sorrentino et al.

It is certified that error appears in the above-identified patent and that said Letters Patent is hereby corrected as shown below:

In the Claims

On Column 21, Claim 1, Line 6: CD4-CD8-CD25+CD4430 should read:
-- CD4-CD8-CD25+CD44+ --;

On Column 21, Claim 1, Lines 10-11: CD4+-CD8+, CD4-CD8+or CD4+CD8- should read:
-- CD4+CD8+, CD4-CD8+ or CD4+CD8- --;

On Column 21, Claim 1, Line 15: (DN1), (D2), CD4-CD8-CD44- CD25+(DN3), should read:
-- (DN1), (DN2), CD4-CD8-CD44-CD25+ (DN3), --.

Signed and Sealed this
Fourteenth Day of June, 2022

*Katherine Kelly Vidal*

Katherine Kelly Vidal
*Director of the United States Patent and Trademark Office*

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 1
ccaatcagtt cgcttctc                                                    18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctgcttctcg cttctgttc                                                   19

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
agtagtgtgt gcccgtctgt                                                  20

<210> SEQ ID NO 4
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aatgatacgg cgaccaccga gatctacact ctttccctac acgacgctct tccgatctgc      60
tgtttgcatc cgaatc                                                      76

<210> SEQ ID NO 5
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatgatacgg cgaccaccga gatctacact ctttccctac acgacgctct tccgatctgt      60
ggtctcgctg ttcctt                                                      76

<210> SEQ ID NO 6
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aatgatacgg cgaccaccga gatctacact ctttccctac acgacgctct tccgatctga      60
tccctcagac cctttagt                                                    79
```